United States Patent [19]

Hayashi et al.

[11] Patent Number: 5,164,159
[45] Date of Patent: Nov. 17, 1992

[54] AUTOMATED SYNTHESIZING APPARATUS

[75] Inventors: Nobuyoshi Hayashi, Kawanishi; Tohru Sugawara, Osaka, both of Japan

[73] Assignee: Takeda Chemical Industries, Ltd., Osaka, Japan

[21] Appl. No.: 321,748

[22] Filed: Mar. 10, 1989

[30] Foreign Application Priority Data

Mar. 11, 1988 [JP] Japan .................. 63-59004

[51] Int. Cl.$^5$ .................. G05D 7/00; G01N 35/00; G05B 1/06
[52] U.S. Cl. .................. 422/81; 422/100; 203/3; 203/DIG. 2; 364/500
[58] Field of Search .................. 422/62, 70, 130, 188, 422/189, 100, 196, 202, 225, 81; 436/50, 55, 178; 364/500; 203/2, 3, DIG. 2, DIG. 6; 159/44, 25.2; 210/93, 515

[56] References Cited

U.S. PATENT DOCUMENTS

| | | | |
|---|---|---|---|
| 3,321,280 | 5/1967 | Trotter, Jr. et al. | 422/62 |
| 3,459,304 | 8/1969 | Brenchley | 210/93 |
| 3,794,566 | 2/1974 | Raal | 203/3 |
| 3,951,741 | 4/1976 | Pfaender et al. | 422/62 |
| 4,250,159 | 2/1981 | Cowley | 436/55 |
| 4,283,202 | 8/1981 | Friis-Hansen | 436/55 |
| 4,302,421 | 11/1981 | Baker | 422/63 |
| 4,472,355 | 9/1984 | Hickam et al. | 422/62 |
| 4,488,239 | 12/1984 | Agarwal | 422/62 |
| 4,598,049 | 7/1986 | Zelinka et al. | 435/287 |
| 4,621,062 | 11/1986 | Stewart et al. | 436/55 |
| 4,701,304 | 10/1987 | Horn et al. | 422/62 |
| 4,746,490 | 5/1988 | Saneii | 422/62 |
| 4,798,798 | 1/1989 | Mehnert et al. | 422/62 |
| 4,802,981 | 2/1989 | Kenney et al. | 422/70 |
| 4,835,707 | 5/1989 | Amano et al. | 422/62 |
| 4,920,056 | 4/1990 | Dasgupta | 436/50 |

FOREIGN PATENT DOCUMENTS 0156588   3/1985   European Pat. Off. .
59-216830 12/1984   Japan .
2161815A  1/1986   United Kingdom .

OTHER PUBLICATIONS

Zenie, F. H., "Trends in Laboratory Automation-Technology and Economics", Advances in Laboratory Automation Robotics-1984, Zymark Corporation, Hopkinton, MA, pp. 1-16.

"Erstellen von Ablaufsteuerungen fur Chargenprozesse mit wechselnden Rezepturen", Automatisierungstechnische Praxis 29(1987) No. 1.

*Primary Examiner*—W. Gary Jones
*Assistant Examiner*—Todd J. Burns
*Attorney, Agent, or Firm*—Wenderoth, Lind & Ponack

[57] ABSTRACT

An automated computer controlled synthesizing apparatus which includes a raw material, reagent and solvent supply unit, a reaction unit, a purification unit provided with HPLC and CPC, and a freeze-drying unit for freeze-drying a purified product supplied from the purification unit. The raw material, reagent and solvent supply unit includes a plurality of reservoirs for containing raw material, reagents and solvents; volumetric tubes and gas-liquid boundary sensors for the quantification of the raw materials, reagents and solvents from the reservoirs; flow-lines for supplying the raw material, reagent and solvent from the reservoirs towards subsequent steps; and solenoid valve assemblies disposed on the respective flow-lines for selectively closing and opening such respective flow-lines. The reaction unit includes a reaction flask device adapted to receive the raw material, reagent and solvent from the raw material, reagent and solvent supply units respectively, a separation funnel for extracting or washing a product which is transferred from the reaction flask device; a pH adjusting flask for adjusting acidity or basicity of the product liquid from the separation funnel; and a plurality of reagent reservoirs disposed for adding a predetermined quantity of reagent to the reaction flask device, volumetric tubes and gas-liquid boundary sensors.

6 Claims, 18 Drawing Sheets

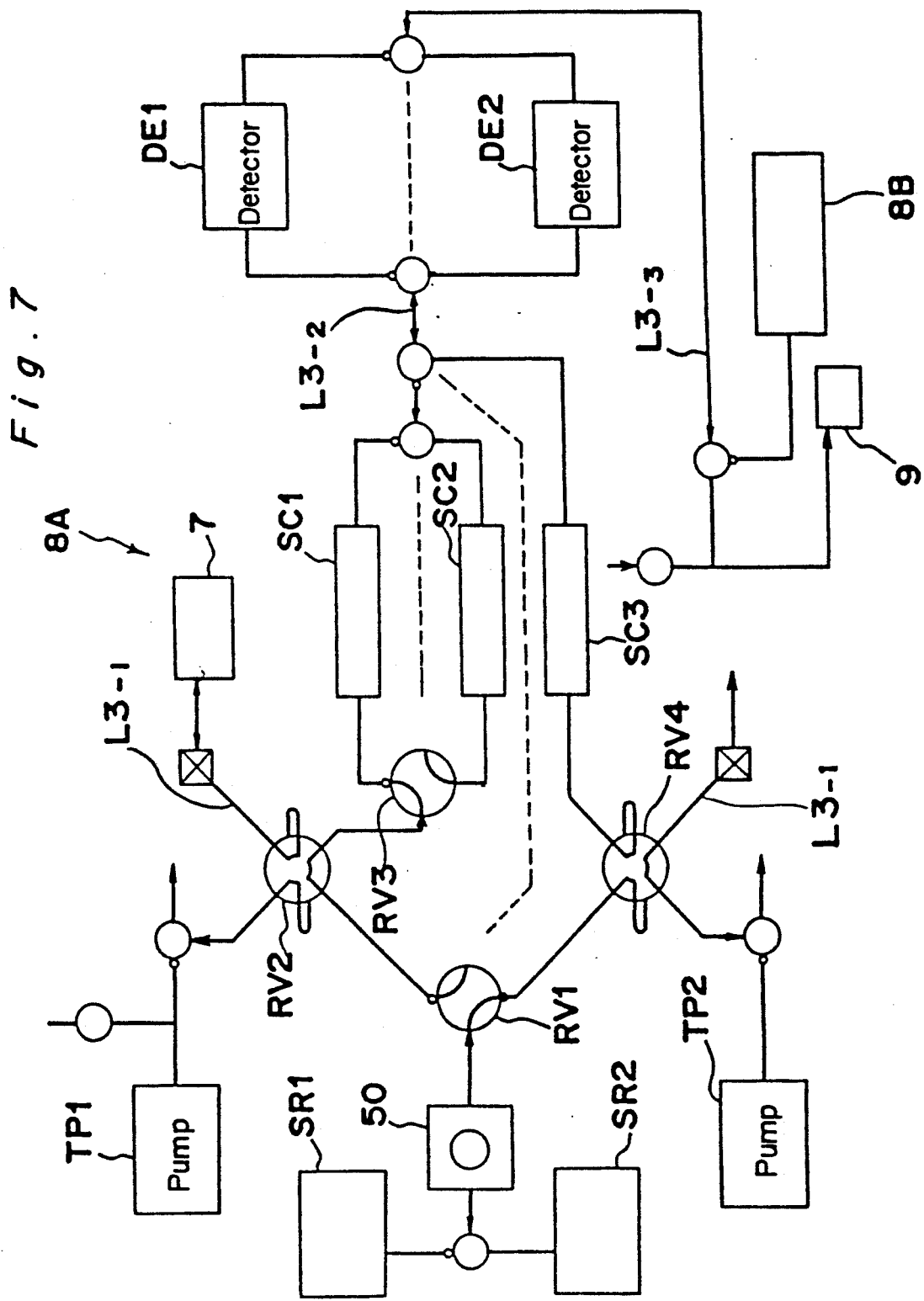

AUTOMATED SYNTHESIZING APPARATUS

BACKGROUND OF THE INVENTION

1. Field of the Invention

The present invention generally relates to an automated synthesizing apparatus and, more particularly, a computer-assisted automated synthesizing apparatus for the automated synthesis of a plurality of derivatives of particular chemical composition such as the synthesis of substituted N-(carboxyalkyl)amino acids and their derivatives.

2. Description of the Prior Art

In pharmaceutical research it is often necessary to synthesize many derivatives of one particular active compound to seek out the relationship between the chemical structure and the biological activity.

Although at an early stage of research automation utilizing an automated batch-type reaction device has been developed, it has generally been aimed at automation of bench-scale reactions to determine the best synthetic routes or optimum reaction conditions prior to pilot-scale work.

However, the conventional instruments are rarely equipped with automated systems for purification and isolation of the products, and furthermore, the reaction optimization often utilizes analytical techniques which require relatively time consuming measurement such as, for example, HPLC. Because of the foregoing, the conventional instruments for syntheses with rapid and/or multi-step reactions, especially those with unstable or undetectable intermediates, has not been automated satisfactorily. Hence, a relatively large amount of man power has hitherto been required in performing those jobs which are essential for pharmaceutical research.

SUMMARY OF THE INVENTION

The present invention has been developed with due regard to the foregoing prior art technology and has as its essential object the provision of an apparatus capable of automatically synthesizing a relatively wide range of compound pounds and also of being used for isolation and purification of the compounds.

In order to accomplish the above described object, the present invention provides an automated synthesizing apparatus which comprises a raw material, reagent and solvent supply unit, a reaction unit, a purification unit provided with a device such as, for example, HPLC (high performance liquid chromatography) or CPC (centrifugal partition chromatography), and a freeze-drying unit for freeze-drying the purified products supplied from the purification unit. The raw material, reagent and solvent supply unit comprises one or a plurality of reservoirs for containing raw material, reagents and solvents; volumetric tubes equipped with a gas-liquid boundary sensors for the quantification of the raw material, reagents and solvents from the reservoirs; flow-lines for supplying the raw material, reagent and solvent from the reservoirs towards subsequent steps; and solenoid valve assemblies disposed on the respective flow-lines for selectively closing and opening such respective flow-lines.

The reaction unit comprises a reaction flask device adapted to receive the raw material from the raw material, reagent and solvent supply unit; a separation funnel for extracting and washing a product which is transferred from the reaction flask device; a pH adjusting flask for adjusting the acidity or basicity of the reaction liquid from the separation funnel; a plurality of reagent reservoirs disposed for adding a predetermined quantity of reagent to the reaction flask device, volumetric tubes and gas-liquid boundary sensors.

In accordance with the present invention, all of the units, the sensors and the solenoid valve assemblies referred to above are so connected with a computer that the sequence of operation thereof can be controlled by the computer.

According to another preferred embodiment of the present invention, an automated synthesizing apparatus comprises a supply unit which comprises a plurality of reservoirs containing raw material, reagents, solvents, pH adjusting liquid, etc., means for automatically supplying the liquids from source baths to the reservoirs, volumetric tubes and sensors for quantifying the liquids from the reservoirs, flow lines connecting the reservoirs to subsequent processing steps, and solenoid valves disposed on the flow lines for selectively opening and closing passages; a reaction unit which comprises the plurality of reaction flasks and pH adjusting flasks, flow lines capable of allowing the liquids to be supplied from selected ones of the reservoirs of the supply unit, flow lines capable of allowing recirculation among the reaction flasks and between the reaction flasks and the pH adjusting flasks, an extraction/separation funnel and a drying tube circulatorily disposed among the flasks through flow lines, a monitoring HPLC for the analysis of a reaction liquid, which HPLC is connected with the reaction flasks through flow lines, and solenoid valves disposed one on each of the flow lines; a purification unit provided with a purification HPLC and/or CPC connected with the reaction flasks and the pH adjusting flasks of the reaction unit through flow lines; and a fraction collector connected with the purification unit for collecting purified products and for supplying arbitrary portion of the purified products to the reaction flasks of the reaction unit through flow lines.

In a further preferred embodiment of the present invention, the apparatus comprises a services unit including a heating medium/cooling medium circulating unit for supplying a heating medium or a coolant for heating or cooling the reaction flask disposed in the above described unit, a wash-solvent supply unit for washing various components of the above described units and the flow-lines, and an exhaust/drainage unit for exhausting the above described wash-solvent and other wastes.

In a further preferred embodiment of the present invention, the reaction flask device is provided with a jacket provided at an outer periphery thereof for heating or cooling it and has a gap between the flask and the jacket for the circulation of the heating medium or the coolant. The flask is provided with stirrer blades for stirring the reaction liquid within the flask and has an opening defined at the top thereof for connection with a pressure reducing means. A vessel which acts as a concentration sensor having an opening through which a thermocouple is inserted is fitted to the flask. By heating the flask and reducing the pressure inside the flask, the reaction liquid can be concentrated, and the end point of the concentration is determined with the thermocouple.

In the practice of the present invention, the reaction flasks may have coolant tubes mounted thereabove in communication therewith so that vapor from the reaction flasks can be condensed, with the resultant liquid being allowed to drop into the flasks. Also, air may be introduced into the reaction flasks to bubble the liquid for the purpose of stirring and/or each of the reaction flasks may be surrounded by a respective oil bath provided with a heater.

Also, it is preferred that a filter may be provided in the vicinity of the drying tubes and valves and/or at portions of the flow lines from which the liquid or air is withdrawn. Again, an extracting device is preferably provided with a temporary storage bottle for the temporary storage since the extraction is carried out repeatedly.

Also, in the purification unit, other than HPLC and CPC, an electrophoresis device, a centrifugal chromatography or a recrystallization device or a combination thereof can be employed in the practice of the present invention. By way of example, arrangement may be preferably made wherein, while two purification devices such as HPLC and CPC are provided, the reaction liquid can be selectively or continuously supplied to HPLC and CPC.

According to the present invention, the automated synthesizing apparatus comprises a series of units including the raw material, reagent and solvent supply unit, the reaction unit, the purification unit and the freeze-drying unit and the services unit, all of those units being automatically controlled by the computer to efficiently produce many derivatives of one particular compound structure with no need for manual intervention.

BRIEF DESCRIPTION OF THE DRAWINGS

The above and other objects and features of the present invention will become clear from the following description taken in conjunction with a preferred embodiment thereof with reference to the accompanying drawings, in which:

FIG. 7 is a schematic diagram showing the structure of an HPLC device;

DETAILED DESCRIPTION OF THE EMBODIMENT

Figure 1:
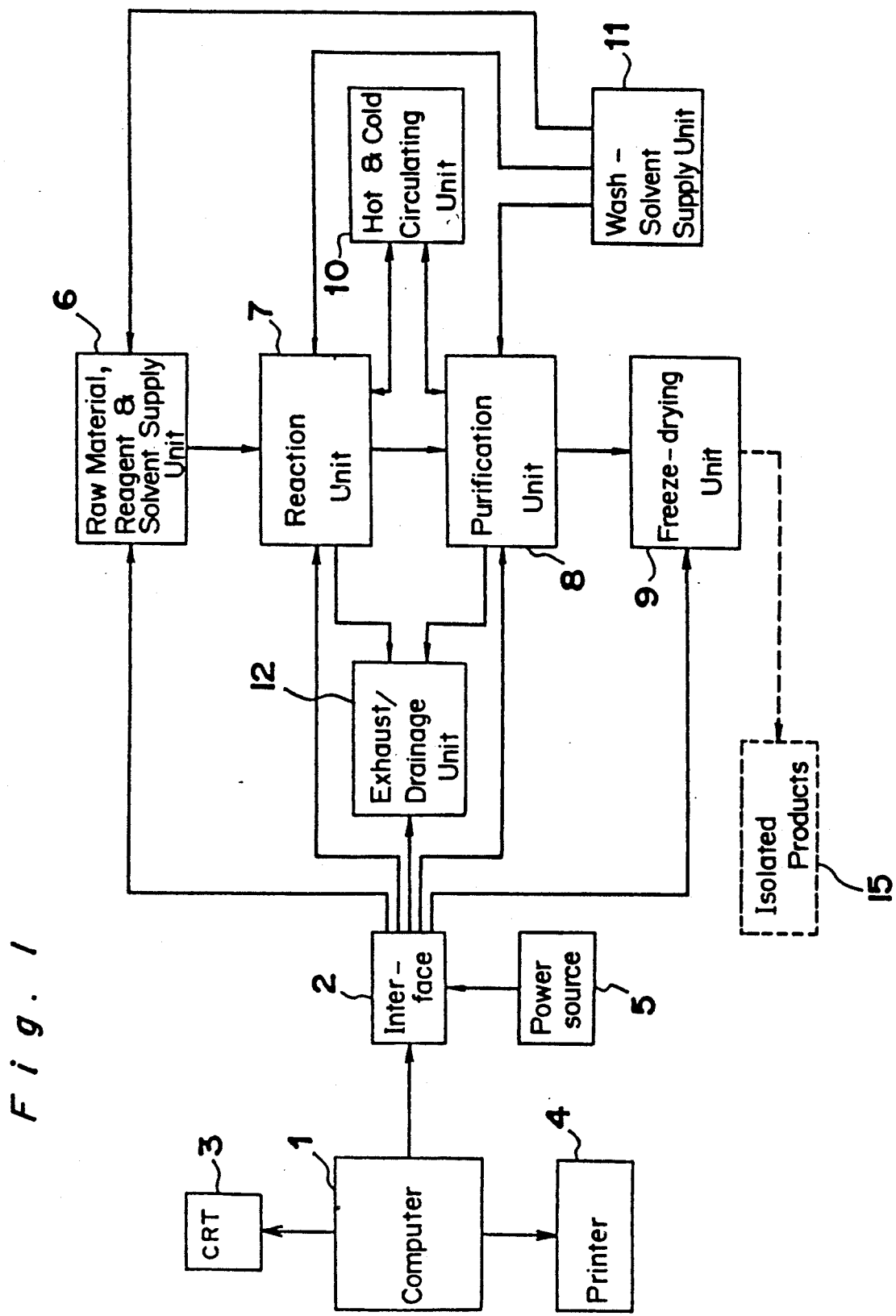
FIG. 1 is a block circuit diagram of an automated synthesizing apparatus of the present invention.

Before the description of the present invention proceeds, it is to be noted that like parts are designated by like reference numerals throughout the accompanying drawings. It is also to be noted that, throughout the accompanying drawings, particularly in those which illustrate fluid circuits, the symbols ◯ represent a solenoid valve and the symbols ⊠ represent a gas-liquid or liquid-liquid boundary sensor.

FIRST PREFERRED EMBODIMENT

An automated synthesizing apparatus according to a first preferred embodiment of the present invention generally comprises a computer system and a synthesis system. The computer system comprises, as best shown in FIG. 1, a computer 1 and an interface 2, the computer 1 being connected with a CRT monitor 3 and a printer 4 while the interface 2 is connected to a main electric power source 5.

The above described computer system is also employed in the practice of a second preferred embodiment of the present invention which will be described later, and is used to control the various functions.

Figure 2:
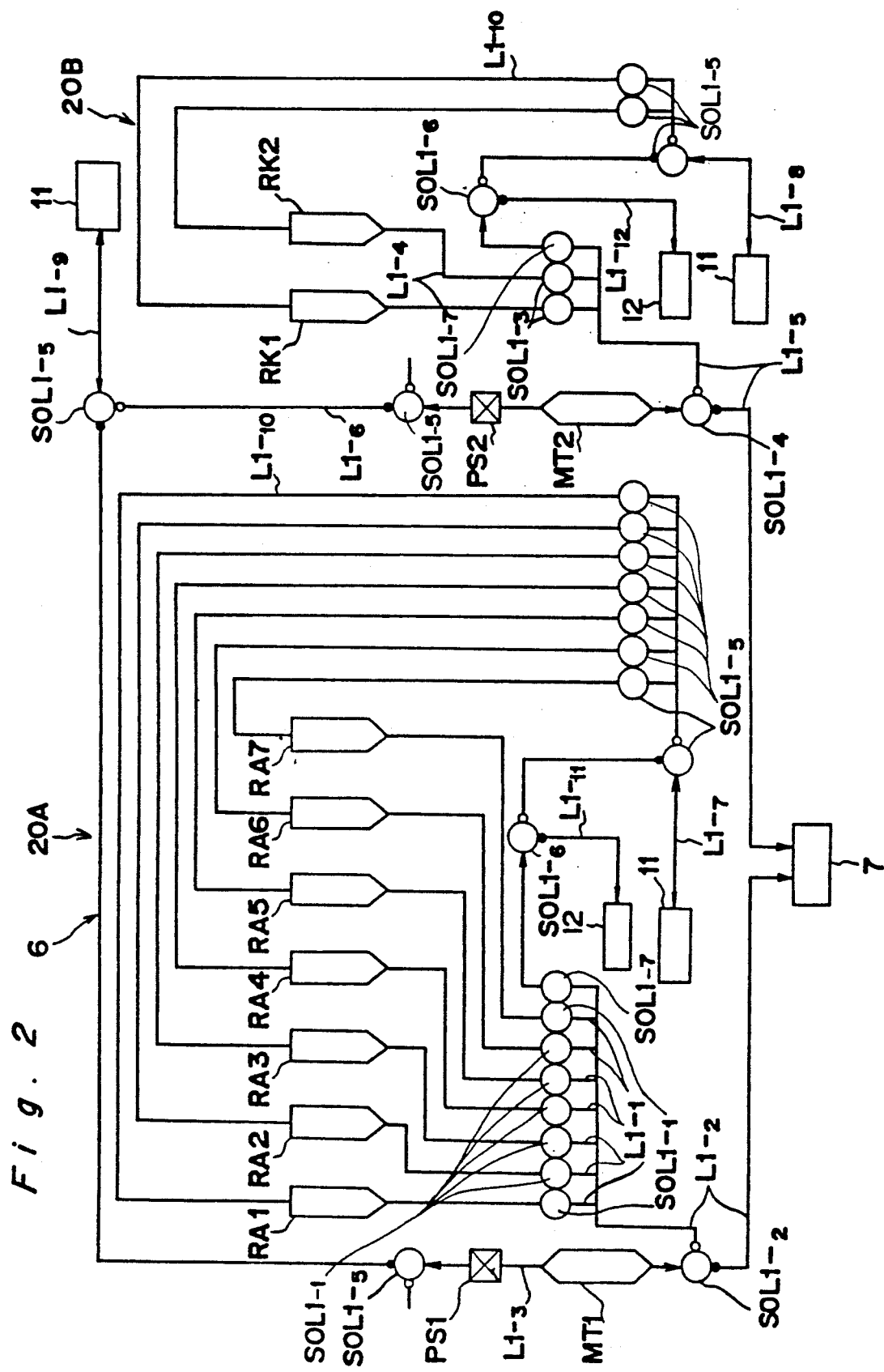
FIG. 2 is a schematic diagram showing the structure of a raw material, reagent and solvent supply unit.

According to the first preferred embodiment of the present invention, the automated synthesizing apparatus shown in FIG. 1 comprises, as shown in FIG. 2, a raw material, reagent and solvent supply unit 6, a reaction unit 7, a purification unit 8, a freeze-drying unit 9, a heating medium/cooling medium circulating unit 10, a wash-solvent supply unit 11 and an exhaust/drainage unit 12.

In the first embodiment of the present invention, a final product given by the automated synthesizing apparatus is directed mainly to a water-soluble product and the apparatus is so designed that various procedures take place sequentially in one way in order from the supply unit 6, the reaction unit 7, the purification unit 8 and the freeze-drying unit 9 to give a final product 15, which is a powdered synthesized material.

All of the above described hardware units 6 to 12 are connected, through the interface 2, to the computer 1, which forms a control unit, so that all of these units can be controlled and operated according to a program stored in a diskette of the computer 1. Each of service units such as the heating medium/cooling medium circulating unit 10, the wash-solvent supply unit 11 and the exhaust/drainage unit 12, the reaction unit 7 and the purification unit 8 can be controlled to accomplish the reaction and purification and isolation of a product 15 via the freeze-drying unit 9.

The details of each of the various units will now be described individually.

Referring to FIG. 2, the raw material, reagent and solvent supply unit 6 comprises two separate supply devices 20A and 20B from which different raw material is supplied in a different predetermined volume. The supply device 20A includes one or a plurality of, for example, seven, reservoirs RA1 to RA7 for containing raw material A such as, for example, amino acid derivatives, and the supply device 20B includes two reservoirs RK1 and RK2 for containing raw material B such as, for example, keto-acids. The raw material A is quantified to, for example, 5 ml and the raw material B is quantified to, for example, 10 ml, these predetermined quantities of the raw material A and B being supplied to a first reaction flask RF1 which forms a part of the subsequent reaction unit 7. An identical volume of these solutions can be measured by repetition.

In the supply device 20A, the reservoirs RA1 to RA7 are connected to a common supply line $L1_{-2}$ through respective supply lines $L1_{-1}$, the common supply line $L1_{-2}$ being connected to the first reaction flask RF1. The supply lines $L1_{-1}$ have respective solenoid valve assemblies $SOL1_{-1}$ disposed thereon for selectively opening and closing the supply lines, and the common supply line $L1_{-2}$ has a three-way solenoid valve assembly $SOL1_{-2}$ disposed thereon. The three-way solenoid valve assembly $SOL1_{-2}$ is connected with a line $L1_{-3}$ having both of a 5 ml volumetric tube MT1 and a gas-liquid boundary sensor PS1 in the form of a photosensor disposed thereon and operable to supply the raw material A supplied from the reservoirs RA1 to RA7 to the line $L1_{-3}$. However, when the gas-liquid boundary sensor PS1 detects that 5 ml of the raw material has been supplied to the volumetric tube MT1 through the line $L1_{-3}$, the solenoid valve assembly $SOL1_{-2}$ is activated to supply the quantified raw material A to the first reaction flask RF1 of the reaction unit 7.

The supply device 20B is substantially similar to the supply device 20A. In this supply device 20B, supply lines $L1_{-4}$ connected respectively with the reservoirs RK1 and RK2 are connected with the first reaction flask RF1 through a common supply line $L1_{-5}$. Solenoid valve assemblies $SOL1_{-3}$ and $SOL1_{-4}$ are disposed respectively on the supply lines $L1_{-4}$ and the common supply line $L1_{-5}$. The solenoid valve assembly $SOL1_{-4}$ is connected with a line $L1_{-6}$ having both of a 10 ml volumetric tube MT2 and a gas-liquid boundary sensor PS2 disposed thereon so that the raw material B can be quantified to 10 ml and can then be supplied to the first reaction flask RF1.

All of the reservoirs RA1 to RA7, RK1 and RK2 and the volumetric tubes MT1 and MT2 are adapted to be washed with water and methanol alternately directed thereto and, for this purpose, the lines $L1_{-1}$ to $L1_{-6}$ are connected with lines $L1_{-7}$ to $L1_{-9}$, connected with the wash-solvent supply unit 11, through a solenoid valve assembly $SOL1_{-5}$ and a wash-solvent supply line $L1_{-10}$. Also, for the purpose of exhausting the washing liquid to the exhaust/drainage unit 12, the above described lines are connected with exhaust lines $L1_{-11}$ and $L1_{-12}$ through a solenoid valve assembly $SOL1_{-6}$. It is to be noted that all of the above described lines form part of a closed system.

It is to be noted that 29 solenoid valve assemblies $SOL-1$ to $SOL1_{-6}$ and the two sensors PS1 and PS2 referred to above are controlled by the computer 1 and this is to be understood as applicable to the other solenoid valve assemblies as well as the other sensors which are mentioned in the following description.

Figure 3:
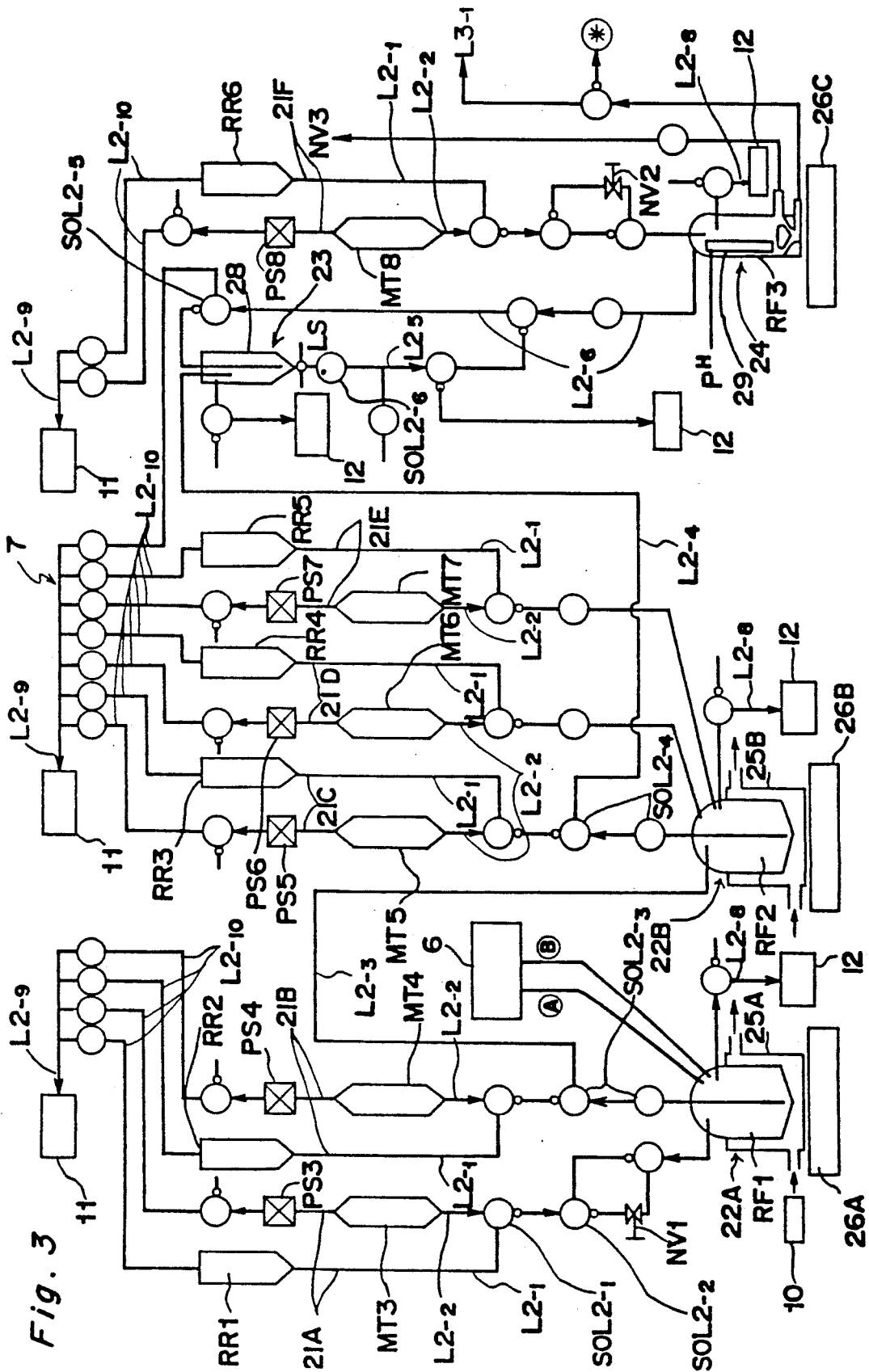
FIG. 3 is a schematic diagram showing the structure of a reaction unit.

The details of the reaction unit 7 are best shown in FIG. 3. As shown therein, the reaction unit 7 comprises two series of reaction systems and one pH adjusting system. Namely, the reaction unit 7 comprises six reagent supply devices 21A to 21F, two reaction flask devices 22A and 22B, a separation funnel device 23 provided with a liquid-liquid boundary sensor LS, and a pH adjusting flask device 24 having one pH electrode.

The first and second reaction flask devices 22A and 22B are of generally identical construction and include first and second flasks RF1 and RF2 of 100 ml in volume provided externally with respective circulating jackets 25A and 25B, connected with the heating medium/cooling medium circulating unit 10, for the circulation of the heating medium or the coolant therethrough to keep the interiors of the flasks at respective desired temperatures. The heating medium or the coolant may be, for example, 50% aqueous polyethylene glycol. These jackets 25A and 25B retaining the associated flasks are mounted on respective stirrers 26A and 26B so that the reaction liquid supplied to the flasks RF1 and RF2 of the reaction flask devices 22A and 22B can be stirred while kept at a predetermined temperature.

Figure 4:
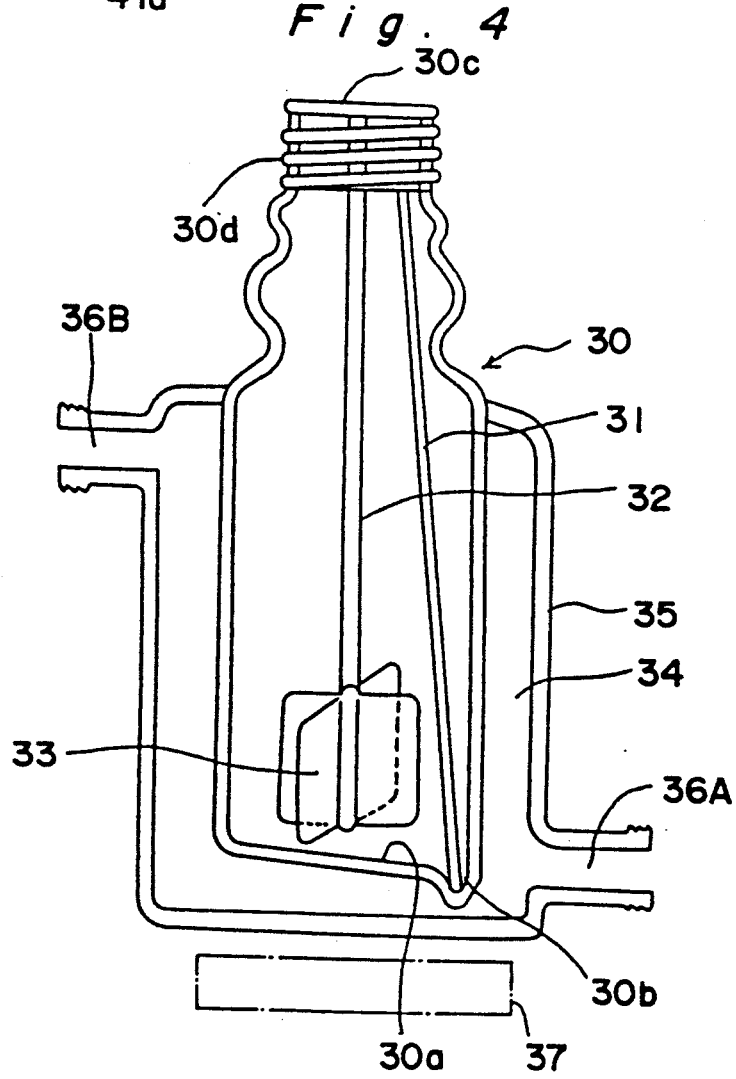
FIG. 4 is a longitudinal sectional view of a reaction flask device.

The details of each of the reaction flask devices 22A and 22B are best shown in FIG. 4. As shown, each flask device 22A or 22B comprises a flask 30 of such a shape as shown and has its bottom 30a inclined moderately downwards said recess 30b being operable to accommodate a residue. The flask 30 also has an upper opening 30c through which both a take-out tube 31 for the removal of the residue collected at the recess 30b and a flexible stirrer shaft 32 are inserted into the interior of the flask 30, the stirrer shaft 32 extending generally coaxially with the longitudinal axis of the flask 30. A lower end of the stirrer shaft 32 situated inside the flask 30 is provided with magnetic stirrer blades 33. The body of the flask 30, including the bottom 30a is surrounded by a jacket 35 with an annular space 34 defined therebetween so as to render the flask as a whole a generally double-walled structure. The jacket 35 has a lower portion having an inlet port 36A defined therein for the introduction of the heating or cooling medium and an upper portion having an exit port 36B defined therein for the discharge of the heating or cooling medium.

Positioned beneath the bottom of the jacket 35 is a permanent magnet with a motor 37 which, when supplied with an electric current, causes the stirrer blades 33 to rotate under the influence of magnetism to accomplish a stirring action.

Figure 5:
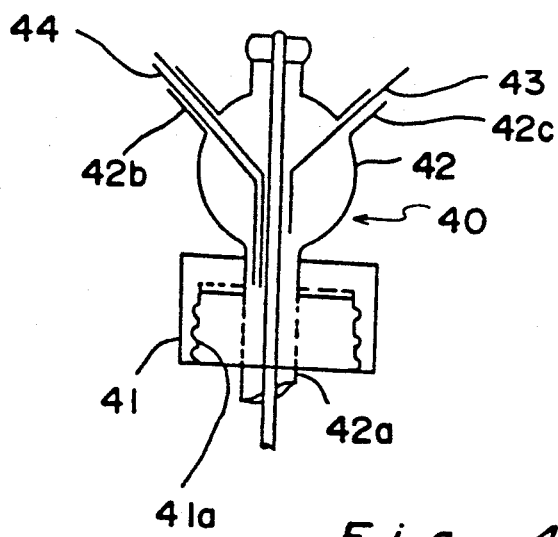
FIG. 5 is a schematic diagram showing the structure of a cap-like assembly with a concentration sensor to be fitted to the reaction flask.

A mouth of the flask 30 adjacent the upper opening 30c is formed with a helical groove 30d over which a cap-like assembly 40 including a concentration sensor 43 shown in FIG. 5 can be removably mounted.

Referring to FIG. 5, the cap-like assembly 40 and the concentration sensor 43 comprises a screw cap 41 having an internal thread 41a for engagement with the helical groove 30d in the flask 30, and also has a vessel 42 mounted thereon. The vessel 42 has a guide tube 42a extending from the bottom thereof and also extending through the sensor cap 41 for insertion into the flask 30. The vessel 42 also has a pair of guide tubes 42b and 42c extending upwards from an upper portion thereof. A vacuum tube 44 connected with a pressure reducing means (not shown) is inserted into the vessel 42 through the guide tube 42b for establishing a substantial vacuum inside the flask 30 to concentrate the reaction mixture and also for drawing vapor to the outside from the interior of the flask 30. The concentration sensor 43 for the detection of the presence or absence of the vapor to determine whether or not the concentration has been finished is inserted into the vessel 42 through the guide tube 42c. Since the temperature inside the flasks abruptly increases upon completion of the concentration, the concentration sensor 43 is preferably employed in the form of a thermocouple.

In the reaction unit 7, the flask RF1 of the first reaction flask device 22A is supplied with both 5 ml of the raw material A and 10 ml of the raw material B which have been quantified in the raw material supply unit 6.

The reagent supply devices 21A to 21F of the reaction unit 7 are of generally similar construction and comprise reagent containing reservoirs RR1 to RR6 connected with the respective flasks through supply lines $L2_{-1}$ having respective three-way solenoid valve assemblies $SOL2_{-1}$ disposed thereon, which assemblies $SOL2_{-1}$ are in turn connected with respective lines $L2_{-2}$. The lines $L2_{-2}$ have both volumetric tubes MT3 to MT8 and gas-liquid boundary sensors PS3 to PS8 disposed thereon so that, by the operation of both of the gas-liquid boundary sensors and the volumetric tubes, the associated reagents can be supplied from the reservoirs RR1 and RR2 to the first flask RF1, from the reservoirs RR3 to RR5 to the second flask RF2 and from the reservoir RR6 to a pH adjusting flask RF3.

The supply of the reagent to the first flask RF1 takes place mainly from the reservoir RR1. The reservoir RR2 is similar in structure to the reservoir RR1 and is used when other reagents are required. During the supply of the reagent from the reservoir RR1 to the first flask RF1, a needle valve NV1 disposed on a supply line downstream of the solenoid valve assembly $SOL2_{-2}$ is adjusted so that a predetermined volume of the reagent can be dropwise (at a maximum rate of 0.41 ml/sec) supplied for a predetermined time to control a first-stage reaction taking place within the first reaction flask RF1.

After the raw materials A and B supplied from the raw material supply unit 6 and the reagent supplied from the reservoir RR1 or RR2 have been mixed and reacted with each other within the first flask RF1, the pressure reducing means (not shown) is operated to permit the reaction liquid within the first flask RF1 to be transferred under reduced pressure to the second flask RF2 through a transfer line $L2_{-3}$. At this time, a solenoid valve assembly $SOL2_{-3}$ disposed on the transfer line $L2_{-3}$ is operated to open the transfer line $L2_{-3}$.

By supplying the respective reagents from the reservoirs RR3 to RR5 to the residue (concentrated reaction liquid) obtained in the second flask RF2 held under vacuum, a second reaction such as the addition of reagent, the concentration of the reaction liquid and the addition of reagent is carried out in the second flask RF2.

The second reaction flask RF2 is connected with the separation funnel 28 through a transfer line $L2_{-4}$ via solenoid valve assembly $SOL2_{-4}$ so that a mixed liquid formed within the second reaction flask RF2 can be sucked by a pressure-reducing pump (not shown) for transportation to the separating funnel 28, at which the mixed liquid can be completely separated into two phases. Either the upper phase or the lower phase can be withdrawn by a liquid-liquid boundary sensor LS disposed at a downstream side of the separating funnel 28.

Figure 6:
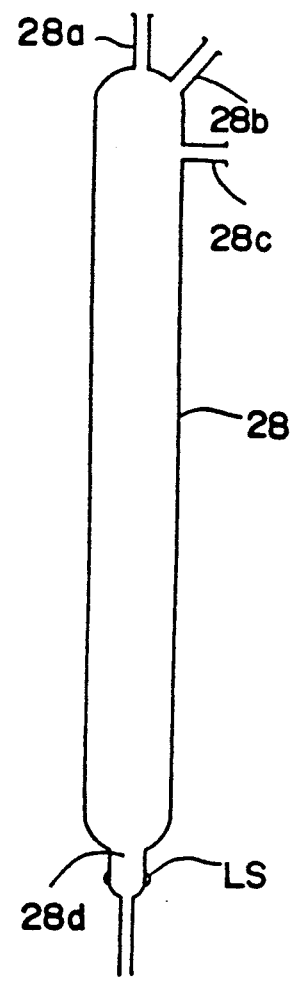
FIG. 6 is a longitudinal sectional view of a separation funnel.

The details of the separating funnel 28 are shown in FIG. 6. The separating funnel 28 is in the form of a generally elongated vessel, 21 mm in diameter and 110 mm in length, and has an upper open end 28a connected with the second reaction flask RF2 through the line $L2_{-4}$ so that the mixed liquid can be supplied into the separating funnel 28 through the open end 28a thereof. The separating funnel 28 also has another upper open end 28b, connected with an upper layer liquid removal tube, and a further upper open end 28c connected with a pressure reducing means for drawing the mixed liquid from the line $L2_{-4}$ into the interior of the separating funnel 28. A lower open end 28d of the separating funnel 28 is connected with a line $L2_{-5}$ for the removal of a lower layer liquid therefrom. The lower open end 28d of the separating funnel 28 is provided with a liquid-liquid boundary sensor LS adapted to be activated by pulse currents for the detection of the liquid-liquid boundary in terms of the difference in electric resistance of the liquid. An electric signal outputted from the liquid-liquid boundary sensor LS is used to control the selective opening and closing of the solenoid valve assemblies $SOL2_{-5}$ or $SOL2_{-6}$ so that a layer of solution forming the upper layer liquid or a layer of organic solvent forming the lower layer liquid can be transported under reduced pressure to the pH flask RF3 through the associated transfer line $L2_{-5}$ or $L2_{-6}$.

The pH adjusting flask RF3 has a pH electrode 29 inserted therein and, also, an internal stirrer connected therein and is mounted on an external magnetic stirrer 26C. A predetermined amount of acid or alkali accommodated in the reservoir RR6 is dropwise supplied into the flask RF3 through a needle valve NV2 to adjust the pH value within the flask RF3. Air is also blown into the flask RF3 through a needle valve NV3 so that, after a slight amount of organic solvent remaining within the flask RF3 has been removed, it can be introduced to the subsequent purification unit 8 (FIGS. 7 and 8).

It is to be noted that, even in the reaction unit 7, as is the case with the raw material supply unit, lines $L2_{-9}$ and $L2_{-10}$ are connected with the wash-solvent unit 11, and a line $L2_{-8}$ is connected with the exhaust/drainage unit 12 for washing these lines.

Figure 8:
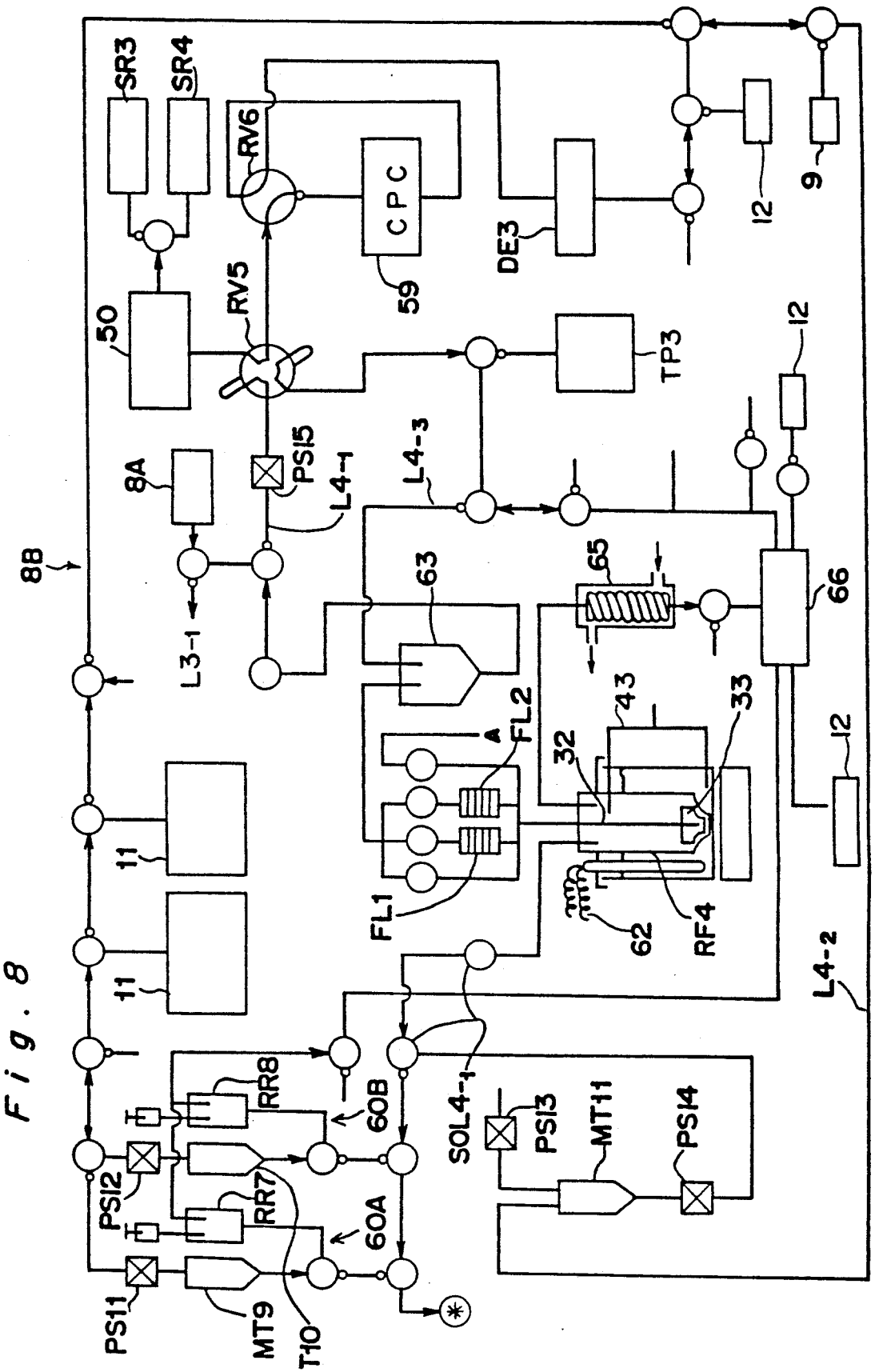
FIG. 8 is a schematic diagram showing the structure of a CPC device and a concentration flask.

The purification unit 8 is comprised of an HPLC device shown in FIG. 7 and a CPC device shown in FIG. 8 which are used either selectively or in series-connected fashion.

As shown in FIG. 7, the HPLC device includes chromatographic columns SC1 to SC3 (columns SC1 and SC2 are for separation and column SC3 is for analysis), an HPLC pump 50, a water supply section SR1, a 50% methanol supply section SR2, transfer pumps TP1 and TP2, a solenoid valve system including six-way rotary valve assemblies RV2 and RV4 and four-way rotary valve assemblies RV1 and RV3, a refractive index detector DE1, a UV absorption detector DE2, etc.

In this HPLC device, in order to avoid entry of air into the HPLC columns SC1 to SC3, it is necessary to remove air from the third flask RF3 of the reaction unit 7 and also from a flow line $L3_{-1}$ extending between the flask and the columns. For this purpose, the transfer pumps TP1 and TP2 are utilized to remove the air remaining within the flow line $L3_{-1}$. Subsequently, after the solvent has been filled from SR1 and SR2 into the flow line, the transfer pumps TP1 and TP2 are reversed to allow, if, for example, the separating columns are used, a sample within the flask RF3 to be drawn into a sample loop fitted onto the six-way rotary valve RV2 so that the sample can be injected from the sample loop into the HPLC column SC1 or SC2. The eluent from the column SC1 or SC2 is supplied via a detector DE1 or DE2 and is, after the refractive index or the UV absorption thereof has been detected, supplied to the CPC device of FIG. 8 or the freeze-drying unit 9 shown in FIG. 9 through a line L3-3. A chromatographic chart given by the above described chromatography can be displayed on the CRT monitor 3 and printed out by the printer 4. Even in the HPLC device, all flow lines are washed with water and methanol and then dried by either a compressed air or an inert gas such as nitrogen, argon, etc., if necessary.

The CPC device is of such a construction as shown in FIG. 8 and includes a CPC 59 for effecting a liquid-liquid separation by means of a centrifugal separator, a six-way rotary valve RV5 provided with a gas-liquid boundary sensor PS15, a four-way rotary valve RV6, a UV detector DE3, a transfer pump TP3, a concentration processing flask RF4, two filters FL1 and FL2, two solvent supply devices 60A and 60B, a condenser 65, etc.

In this CPC device, the eluent from the HPLC device is injected into the CPC through a flow line L4-1 via the rotary valves RV5 and RV6. SR3 and SR4 represent solvent storage tanks and are connected with the CPC 59 through a pump 50. The dissolving solvents are supplied from the storage tanks SR3 and SR4 to the CPC 59. After the ultraviolet absorption has been detected by the detector DE3, the purified product is supplied t the freeze-drying unit 9 for the removal of the isolated product, a fraction collector or to the concentration processing flask RF4 through a line L4-2. Prior to the introduction into the flask RF4, a volumetric tube MT11 is disposed on the line L4-2 and, therefore, after the eluent has been measured (or quantified) to a predetermined volume by the volumetric tube MT11, the solenoid valve SOL4-1 is opened to allow it to be transported to the flask RF4. The flask RF4 is substantially similar in structure with any one of the first and second reaction flasks RF1 and RF2 of the reaction unit 7 as shown in FIGS. 4 and 5 and, therefore, like reference numerals used in FIGS. 4 and 5 are employed for like parts of the flask RF1 for the sake of brevity.

The solvents, contained, in the reservoirs RR7 and RR8 are, measured (or quantified) by associated volumetric tubes MT9 and MT10, injected into the flask RF4. A mixture within the flask RF4 is concentrated while heated by a heater 62, and the timing at which the process is to be terminated is determined by the detection of the presence or absence of vapor with the use of the sensor 43 as hereinbefore described. The concentrate within the flask is processed through the filters FL1 and FL2 and is then stored in a trap 63 before it is subsequently circulated to the CPC through the rotary valve RV5 and RV6 by way of a line L4-1.

The flask RF4 is connected through a condenser 65 with a waste storage vessel 66 for the storage of a waste discharged thereto through the condenser 65.

Even in the CPC device, all flow lines are connected with the wash-solvent supply unit 11 and also with the exhaust/drainage unit 12 so that they can be washed with water and methanol and then dried.

Figure 9:
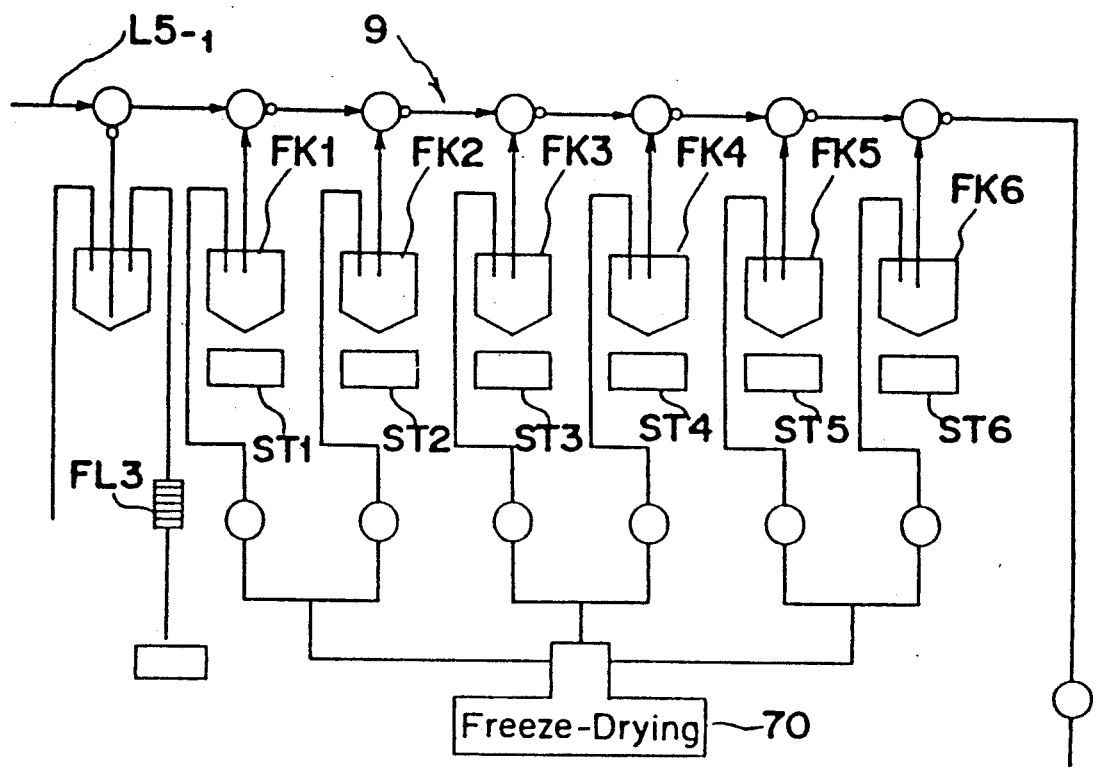
FIG. 9 is a schematic diagram showing the structure of a freeze-drying unit.

The fractionated product purified from the HPLC device is either directly or indirectly through the CPC device is transferred to the freeze-drying unit 9, shown in FIG. 9, and is, after having been introduced into evaporation vessels FK1 to FK6 through a line L5-1, freeze-dried. Each of the vessels FK1 to FK6 has a stirrer ST1 to ST6 positioned therebelow and is connected with a freeze-drier 70.

Figure 10:
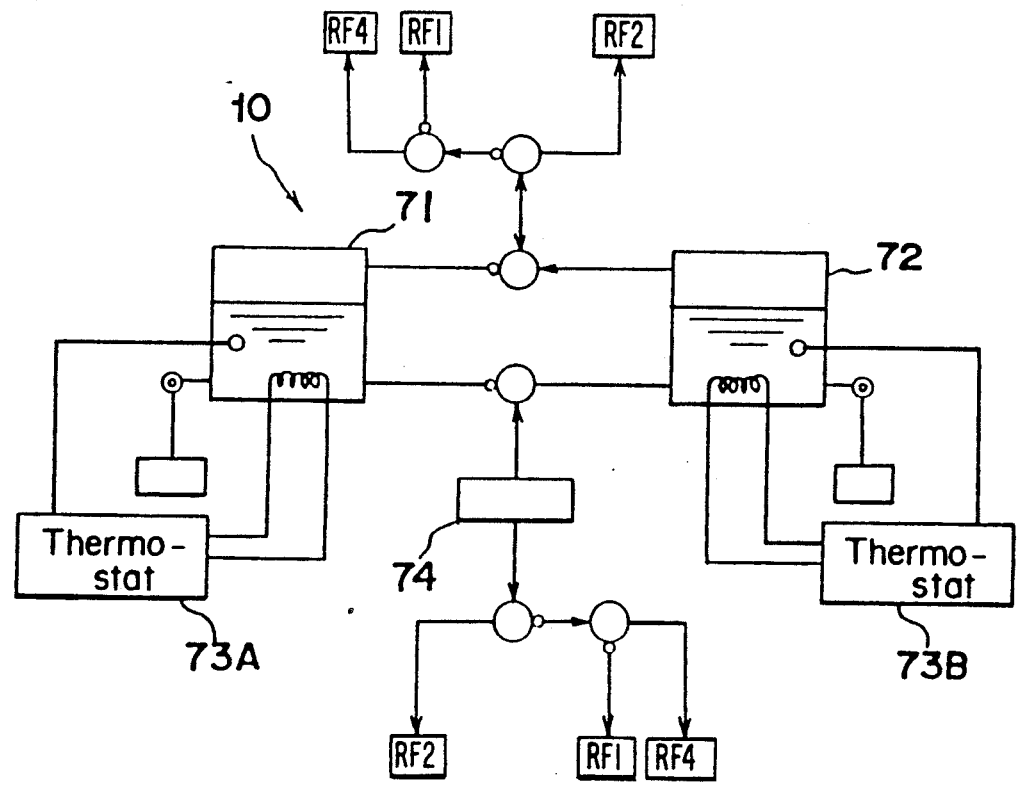
FIG. 10 is a schematic diagram showing the structure of a heating medium/cooling medium supply unit.

The heating medium/cooling medium circulating unit 10 is of the structure as shown in FIG. 10 and comprises a heating medium storage vessel 71 for containing the heating medium, a coolant storage vessel 72 for containing the cooling medium or coolant, thermostats 73A and 73B for controlling the temperature of the associated medias within the vessels 71 and 72, and a pump 74 for pumping one of the heating and cooling media from the associated vessel 71 or 72 to the flasks RF1 to RF4.

Figure 11:
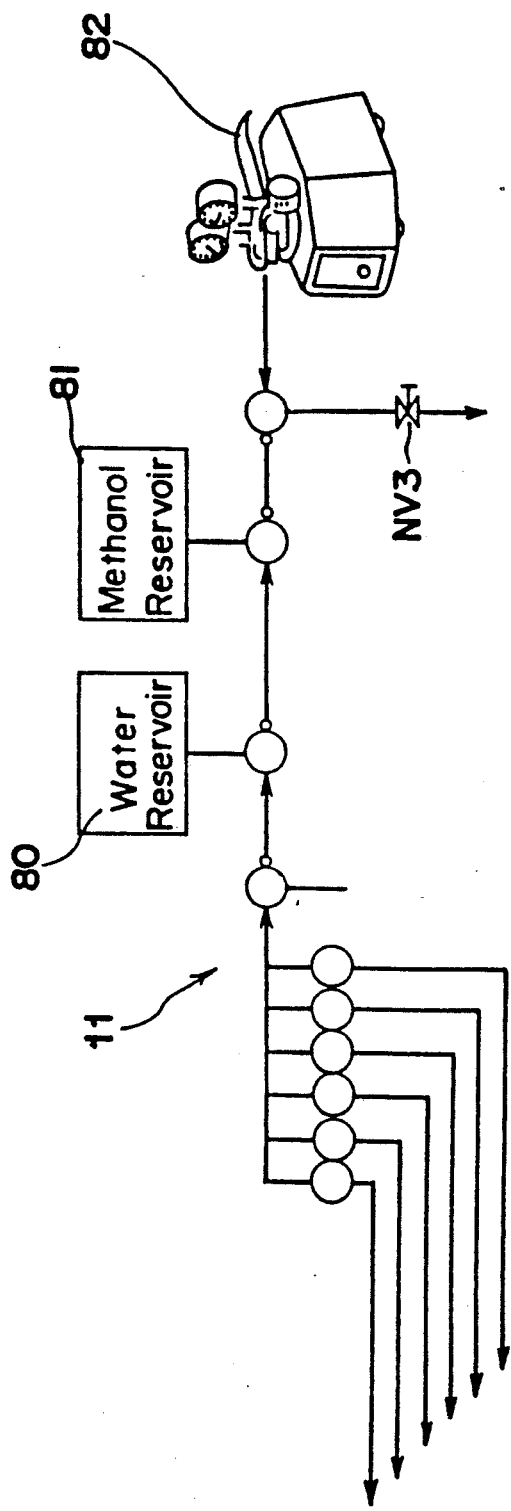
FIG. 11 is a schematic diagram showing the structure of a wash-solvent supply unit.

The wash-solvent supply unit 11 is best shown in FIG. 11 and comprises a water tank 80, a methanol tank 81 and a diaphragm pump 82 for supplying water or methanol from the associated tank 80 or 81 to the various flow lines leading to the various units.

Figure 12:
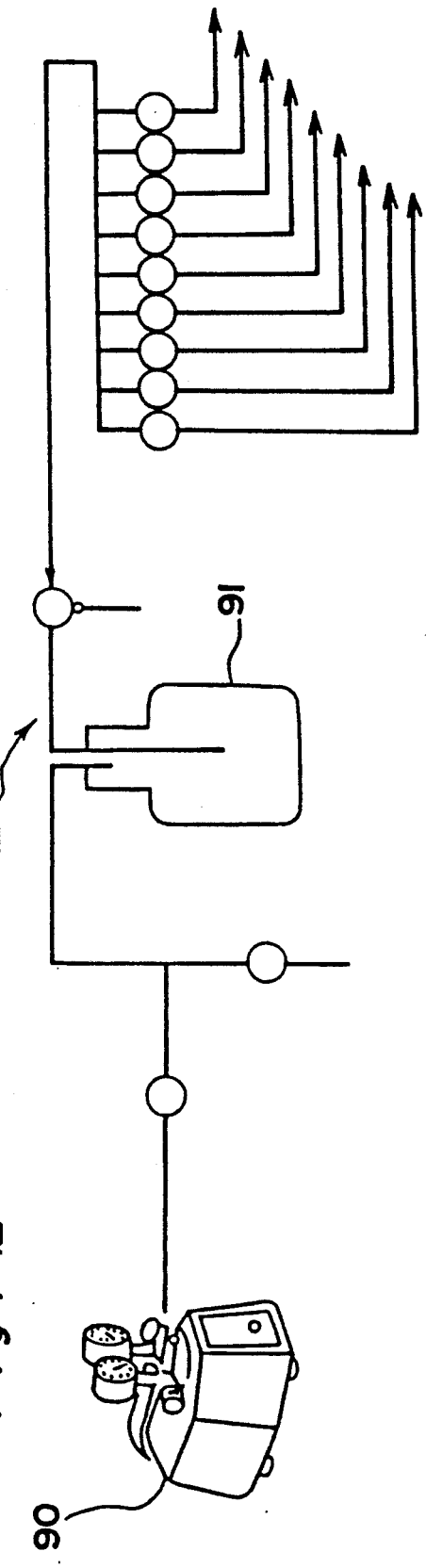
FIG. 12 is a schematic diagram showing the structure of an exhaust/drainage unit.

The exhaust/drainage unit 12 is best shown in FIG. 12 and comprises a diaphragm pump 90 operable to draw liquid medium such as the washing liquid and/or waste gases from the flow lines connected with the various units and to discharge the waste into a waste collecting vessel 91.

Figure 13:
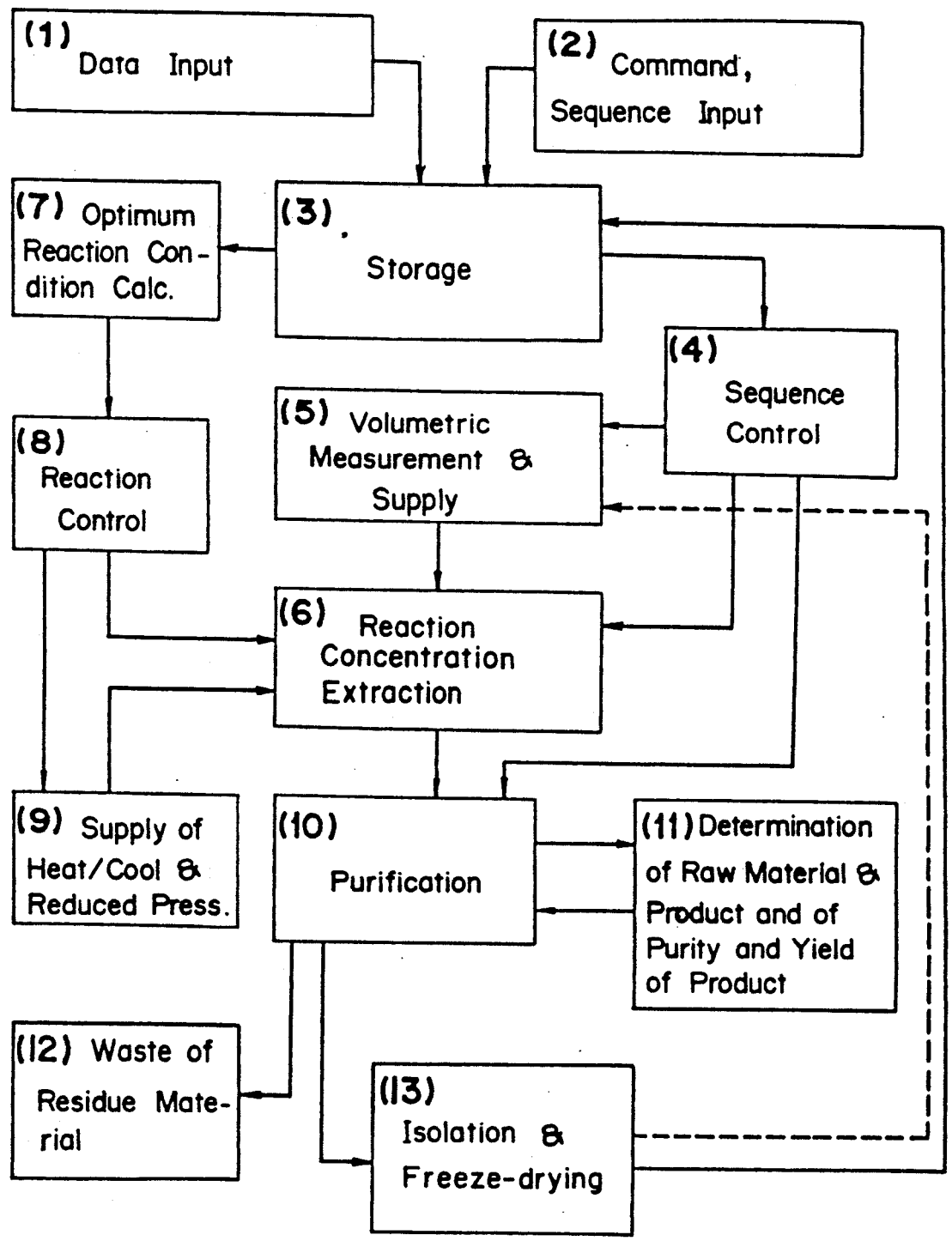
FIG. 13 is a flow chart showing the sequence of control performed by a computer of the automated synthesizing apparatus.

The sequence of operating procedures of supplying the raw material, reagent and solvent, initiating the synthesis reaction, purifying and isolating the resultant product is illustrated in the flow chart of FIG. 13 and is carried out according to a program set up in the computer. Hereinafter, each of the sequential blocks shown in the flow chart of FIG. 13 will be discussed.

Data Input Block (1)

Physical parameters including the concentration of each of the raw materials and reagents, the reaction constants and the substituent constants are inputted to the computer. The physical parameters which have been inputted are automatically called back from a floppy disk.

Command, Sequence Input Block (2)

The numbers of the reservoirs containing the raw material, reagents and solvents are inputted to represent the raw material, reagents and solvents. A combination of the raw material to be reacted and the sequence are specified. The concentration, solvent extraction, the use or non-use of the pH adjusting step, the purifying method (HPLC and/or CPC) and the dissolving solvent are selected.

Storage Block (3) (Computer Memory and Floppy Disk)

The various parameters inputted at the blocks (1) and (2) are all stored in the computer memory and can be called back when required.

Sequence Control Block (4)

Operating commands are generated according to a sequence program.

If the numbers of the reservoirs containing the raw material, reagents and solvents are not inputted at the Command, Sequence Input block (2), the associated supply sequence is skipped to allow the next succeeding operation to take place. The combination and order of the reaction material is uploaded from the input section into a sequence control table. If no concentration input is carried out, the associated procedure in the sequence table is skipped. Where the solvent extraction and the pH adjustment are required, a step of transferring liquid is carried out. The selection of HPLC, CPC and the dissolving solvent is accomplished by switching the associated valves according to an input command.

Volumetric Measurement and Supply Block (5)

In response to signals from the sequence control, the selective opening and closure of the solenoid valve assemblies associated with the raw material, reagent and solvent supply unit 6 and the reaction unit 7 are controlled and, also, the amount of the raw material to be introduced into the reaction flasks is metered according to the output signal from the gas-liquid boundary sensor.

Reaction, Concentration & Extraction Block (6)

Operations associated respectively with the reaction, concentration and extraction in each of the reaction unit 7 and the purification unit 8 are all driven by signals from the sequence control and the reaction control.

Optimum Reaction Condition Calculation (7)

The following general reaction formula corresponds to a variety of substituent constants.

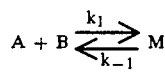

If the rate constant ($k_1$) of reaction to the product M and the equilibrium constant ($k_1/k_{-1}$) are inputted, the reaction constant can be calculated and stored in the storage. From the physical constants stored in the memory, $k_1$ and K for the substituent constants can be calculated.

The concentration of the reaction reagent (R), and the initial concentration and the volume of the mixture of the raw material which have been specified by a command, input section can be called back so that, in combination with $k_1$ and K, the retention time during which the reagent (R) is added during the reaction as well as the amount thereof can be calculated.

Reaction Control Block (8)

The rate at which the reagent is added as determined at the block (7) is converted into a pulse signal which is in turn used to control the solenoid valve assembly. The concentration and the extraction are executed in response to a command generated as a result of interrogation between the concentration sensor (the thermocouple 43) and the liquid-liquid boundary sensor, respectively. In the event of the absence of the command, the control skips to the next succeeding block.

Heating, Cooling and Reduced Pressure Block (9)

The heating or cooling of the flask is carried out by circulating the heating medium or the cooling medium through the jacket of each of the first and second reaction flasks. In response to a signal indicative of the concentration or the movement of the solution, the associated solenoid valve assembly is controlled and the pressure reducing pump is driven.

Purification Block (10)

The purification unit comprises the HPLC device, the CPC device and a system of concentration and acidic or basic solution adjustment, and the HPLC and CPC can be used either selectively or in a series connected fashion.

Material and Product Judgement Block (11)

The component peak of the eluent eluted from the HPLC or CPC is detected and the same peak as the retention time of the raw material is introduced to the waste collecting section The peak of the purified product is used to calculate the purity and yield of the product by determining the relationship between the intensity of the peak, if there is a peak appearing in the neighborhood, and the retention time.

Where both of the purity and the yield exceed a desired value, the resultant fraction is introduced into an isolation and freeze-drying section. On the other hand, if the purity is lower than the desired value, a signal is generated to the purification section for refinement.

If the yield is lower than an expected value, the resultant fraction is introduced into the isolation section and, at the same time, a signal is generated to the storage for re-starting the synthesizing process.

Waste Block (12)

The raw material fraction, as determined at the block (11), and the wash-solvent for washing the flow lines are all introduced to the waste collecting section.

Isolation and Freeze-drying Block (13)

The resultant fraction is introduced into the evaporation vessels and dried.

As hereinbefore described, in the illustrated apparatus, respective signals from the various sensors installed in the associated units are inputted to the computer so that the computer can control the sequence of operations according to a program uploaded in the computer.

In the apparatus of the present invention, since 15 reservoirs for containing the raw material, reagents and reaction solvents are employed, the combination of the first and second flasks RF1 and RF2 makes it possible to perform the synthesis process including a maximum number of six steps.

In other words, the steps of reaction for the synthesis is as follows.

| A + B + (C) → X | First Step |
| X → Y | Second Step |
| Y → P | Third Step |

The solution reaction shown by the above general formulas, the raw material A and B or an intermediate X formed by adding D to a plurality of compounds A, B and C to react therewith (the first step reaction) is further processed to give F and G (the second step). The resultant Y is added with H and J to react therewith thereby to form P (the third step). D, F, G and J may be any one of the reagent, catalyst and solvent. The product obtained in each of the steps is concentrated under atmospheric or reduced pressure and can be reacted when a reagent is added to the intermediate remaining in the flask.

The finally purified reaction product can be refined by a combination of the solvent extraction, HPLC and CPC and, as shown in FIGS. 7 and 8 showing an HPLC chart of the reaction mixture after the refinement, the final powder can be obtained by detecting the peak of the reaction product except for the raw material system, separating the fraction and transferring to a freeze-drying unit.

EXPERIMENTAL 1

Synthesis of N-carboxymethyl-L-phenylalanine Disodium Salt

A solution of L-phenylalanine tert-butylester acetate in methanol, which was stored in the reservoir RA1 of the supply unit 6 was quantified to a predetermined volume (5 ml, 1.125 g, 4 mmol) by the use of the volumetric tube MT1 and the sensor PSI and was then introduced into the first reaction flask RF1 of the reaction unit 7 through the solenoid valve assembly SOL1-2. Similarly, a solution of glyoxylic acid in 50% methanol, which was stored in the reservoir RK1, was quantified to a predetermined volume (10 ml, 0.368 g, 4 mmol) and was then introduced into the first reaction flask RK1.

Within the first reaction flask RK1, the reaction mixture was stirred at room temperature, to which a solution of sodium cyanoborohydride in methanol which was in the reservoir RR1 of the reaction units and was then quantified to a predetermined volume (20 ml, 0.168 g, 2.68 mmol) was subsequently added dropwise in an hour while controlled by the needle valve NV1 and the computer. After the reaction mixture had been stirred for 10 minutes subsequent to the dropwise addition, the reaction liquid is led by the diaphragm pump into the second reaction flask RF2. To the residue which was obtained by removing the solvent at 50° C. under reduced pressure and subsequently cooling, 95% trifluoroacetic acid having been stored in the reservoir RR3 and subsequently quantified to a predetermined volume (10 ml) with the use of the volumetric tube MT5 was added. After the temperature of the second reaction flask RF2 had been turned to room temperature, the reaction mixture was further stirred for one hour. In a manner similar to the foregoing, after the solvent had been evaporated, the residue was cooled at 0° C. and ethyl acetates (20 ml) and an aqueous solution of 3M-sodium hydroxide (10 ml), which had been stored in the reservoir RR4 and RR5 and subsequently quantified by the use of the volumetric tubes MT6 and MT7, respectively, were added to the residue. The two-layer solution in the second reaction flask RF2 was, after having been stirred for 3 minutes, introduced to the separating funnel 28 using a diaphragm pump. After the two-layer liquid had been allowed to stand in the separating funnel 28 for several minutes and had only the aqueous layer solution was introduced to the third flask RF3 (for the pH adjustment) by the use of the liquid-liquid boundary sensor LS. After the pH value had been adjusted to pH 10, and after a slight amount of ethyl acetate mixed therein had been removed by allowing air to enter for several minutes, the solution was introduced to an initialized partition chromatographic column. In the case of the derivative now under discussion, Amberlite XAD-2 (25×500 mm) was used and eluted with water and, after peaks different from the raw material had been collected and freeze-dried, 0.838 g (73.5%) of N-carboxymethyl-L-phenylalanine disodium salt (hydrate) was obtained in the form of a powder.

Elemental Analysis (for $C_{11}H_{11}NNa_2O_4 \cdot H_2O$):
Calculated: C;46.32, H;4.60, N;4.91%.
Found: C;46.51, H;4.52, N;4.88%.
NMR: 3.03(2H,d,J=7 Hz), 3.25(2H,S), 3.53(1H,d,J=7 Hz), 7.38(5H,br,s)

After dissolving in a slight quantity of water and acidificated with 3M-hydrochloric acid under cooling the disodium salt gives N-carboxymethyl-L-phenylalanine as a colorless needle.

Elemental Analysis (for $C_{11}H_{13}NO_4$):
Calculated: C;59.19, H;5.87, N;6.27%.
Found: C;59.13, H;5.81, N;6.33% .
$[\alpha]^{24}D + 16.1°$ (C=0.97, 1M-chloride)
(Literature +15.67°)

EXPERIMENTAL 2

Synthesis of N-(1-sodioxycarbonyl-n-pentyl)-L-isoleucine tert-butylester

A solution of L-isoleucine tert-butylester acetate in methanol, a solution of sodium 2-ketocaproate in methanol, a solution of sodium cyanoborohydride in methanol and an aqueous solution of 0.8M-sodium hydroxide were contained in the respective reservoirs. While controlled by the computer, the raw materials were quantified to a predetermined amount with the volumetric tube and then introduced into the first reaction flask RF1. Sodium cyanoborohydride solution, which had been quantified to a predetermined volume (20 ml, 2.67 mmol) with the volumetric tube, was added dropwise to the reaction mixture under the control of the computer at room temperature. The reaction mixture was stirred for 20 minutes at room temperature. After the final addition of sodium cyanoborohydride, and then the solvent is evaporated under reduced pressure. The 0.8M-sodium hydroxide solution having been quantified to a predetermined volume (10 ml) with the use of the volumetric tube was added to the residue. The resultant aqueous solution was then injected into the Amberlite XAD-2 column (25×500 mm) and eluted with 50% methanol to give the diastereoisomers of N-(1-sodioxycarbonyl-n-pentyl)-L-isoleucine tert-butylester. When each of the two fractions was freeze-dried, 1.09 g (the combined yield of two diastereoisomers 84%) of a powder thereof was obtained.

First Fraction
Elemental Analysis (for $C_{16}H_{30}NNaO_{4.0.5}H_2O$):
Calculated: C;57.81, H;9.40, N;4.21% .
Found: C;58.01, H;9.30, N;4.18%.
IR(KRr): 3420, 2955, 2930, 1720, 1600, 1580, 1155
$[\alpha]^{24}D$ −19.9° (C=1.14, $H_2O$)
NMR (ppm in $D_2O$)δ: 0.88(3H,t,J=6.85 Hz), 0.90(3H,t,J=7.26 Hz), 0.91(3H,d,J=6.42 Hz), 1.20–1.40(6H,m), 1.40–1.65(2H,m,overlapped), 1.50(9H,s), 1.68–1.80(1H,m), 2.93–2.96(1H,dd,J=6.02 and 7.51 Hz)

Second Fraction
Elemental Analysis (for $C_{16}H_{30}NNaO_4$):
Calculated: C;59.42, H;9.35, N;4.33%.
Found C;59.08, H;9.07, N;4.29%.
IR(KRr): 3420, 3320, 2960, 2930, 1720, 1580, 1145
$[\alpha]^{24}D$ −6.2° (C=095, $H_2O$)
NMR (ppm in $D_2O$)δ: 0.89(3H,t,J=6.76 Hz), 0.92(3H,t,J=7.26 Hz), 0.91(3H,d,J=6.76 Hz), 1.20–1.40(6H,m), 1.40–1.65(2H,m,overlapped), 1.48(9H,s), 1.65–1.80(1H,m), 2.99(1H,t,J=6.35 Hz), 3.16(1H,d,J=5.11 Hz)

SECOND PREFERRED EMBODIMENT

The second preferred embodiment differs from the first preferred embodiment in the following respects.

1. The extraction/drying device is added to the reaction unit and a monitoring HPLC device is also added to the reaction unit, which is operable to analyze at any desired time reaction conditions in each of the reaction flasks.

2.) In the reaction unit, mutual recirculation, not one-way flow, is available among the reaction flasks so that in selected one of the reaction flasks reaction procedures such as heating, cooling and concentration can be repeatedly carried out. Similarly, mutual recirculation is available between each reaction flask and the pH adjusting flask so that the reaction liquid, after the pH adjustment, can be led back t the reaction flasks to repeat the reaction procedures. Also, mutual recirculation is available between each reaction flask and the extraction/drying device so that extracting procedures can be repeated.

3) Each of the reaction flasks of the reaction unit is provided with a coolant tube (a condenser) and also one reaction flask with a temperature-adjustable oil bath is provided. In addition, the apparatus including the reaction unit is provided with filters fitted at appropriate locations where air and/or liquid are introduced.

4) Various raw materials such as reagents, solvents, pH adjusting liquids, etc., are installed only in the supply unit and arrangement has been made that the raw materials, reagents and solvents can be supplied directly to arbitrarily chosen one or ones of the flasks installed in the reaction unit. Also, each of the raw materials, reagents or solvents can be automatically supplied from their storage vessels into each reservoir of the supply unit.

5) In the second preferred embodiment, since the final product is the one soluble with an organic solvent and, therefore, only HPLC for purification is provided in the purification unit. It is, however, to be noted that depending on the type of the final product, a CPC device may be employed in place of the HPLC or both of the CPC and the HPLC may be employed. Also, arrangement has been made that the supply can take place directly to the reaction flasks of the reaction unit without passing through the pH adjusting flask.

6) When the final product is not water-soluble, the use of the freeze-drying unit is dispensed with and, instead, the purification unit is provided with a fraction collector unit for supplying a solution containing the final product directly from the purifying HPLC and for storing it. Also, the solution containing the purified product can be, depending on the necessity, supplied again an arbitrary one or ones of the reaction flasks of the reaction unit.

Hereinafter, the second embodiment of the present invention will be described with particular reference to FIGS. 14 to 22. However, for the sake of brevity, only features which differentiate the second embodiment from the previously discussed first embodiment are described.

Figure 14:
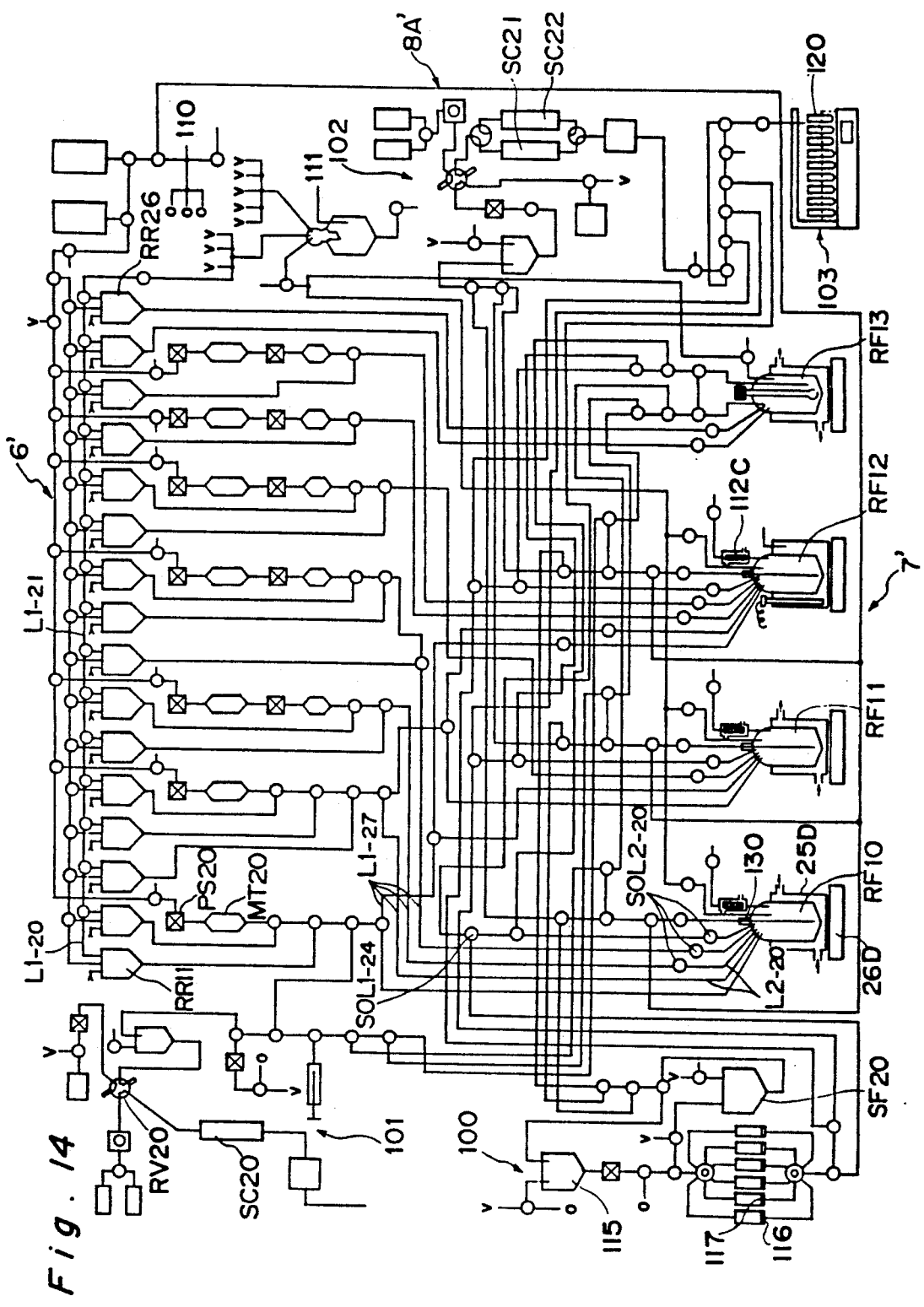
FIG. 14 is a diagram showing the entire system of the synthesizing apparatus according to a second preferred embodiment of the present invention.
Figure 15:
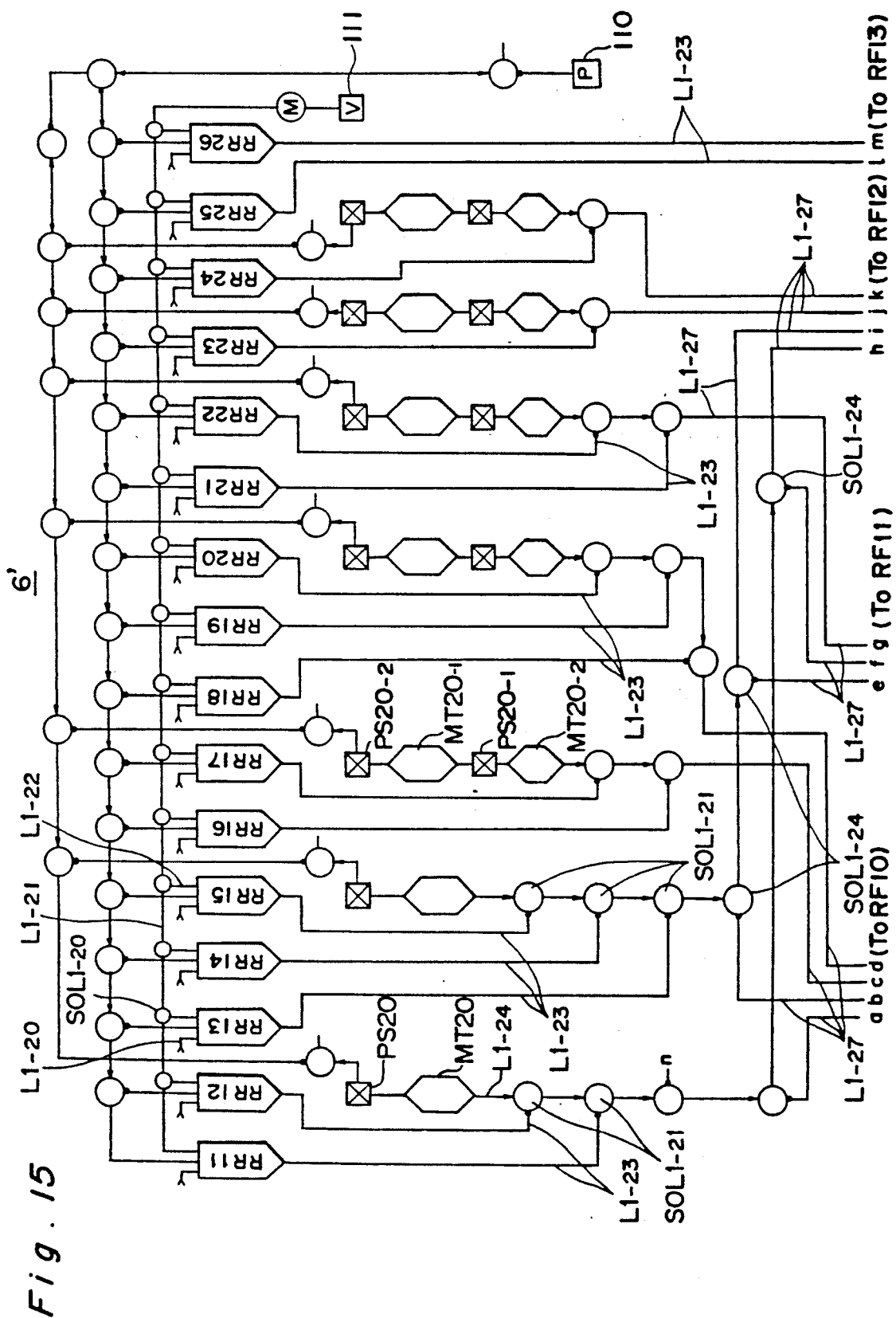
FIG. 15 is a diagram illustrating a supply unit used in the apparatus of FIG. 14.
Figure 16:
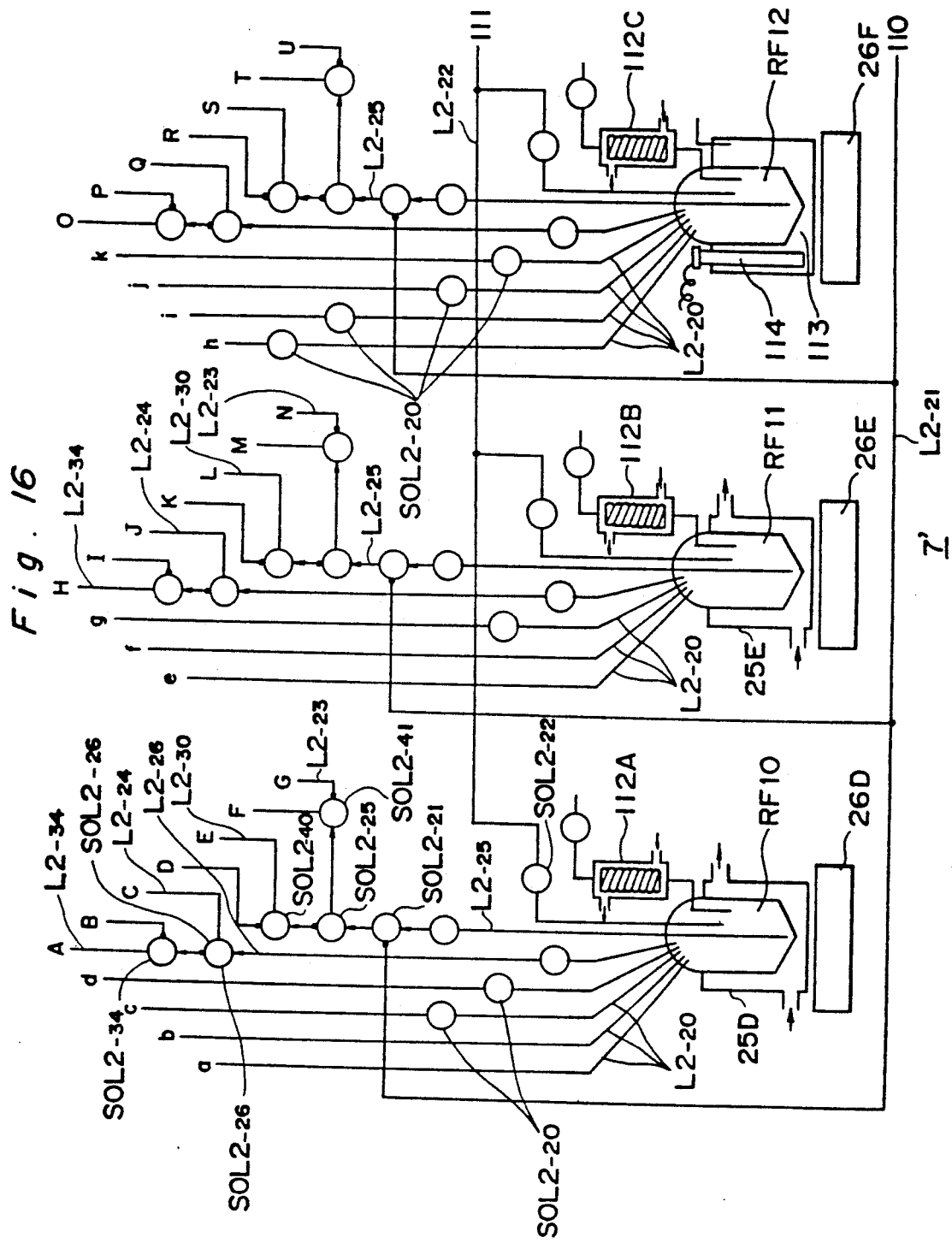
FIG. 16 is a diagram illustrating a plurality of reaction flasks of a reaction unit employed in the apparatus of FIG. 14.
Figure 17:
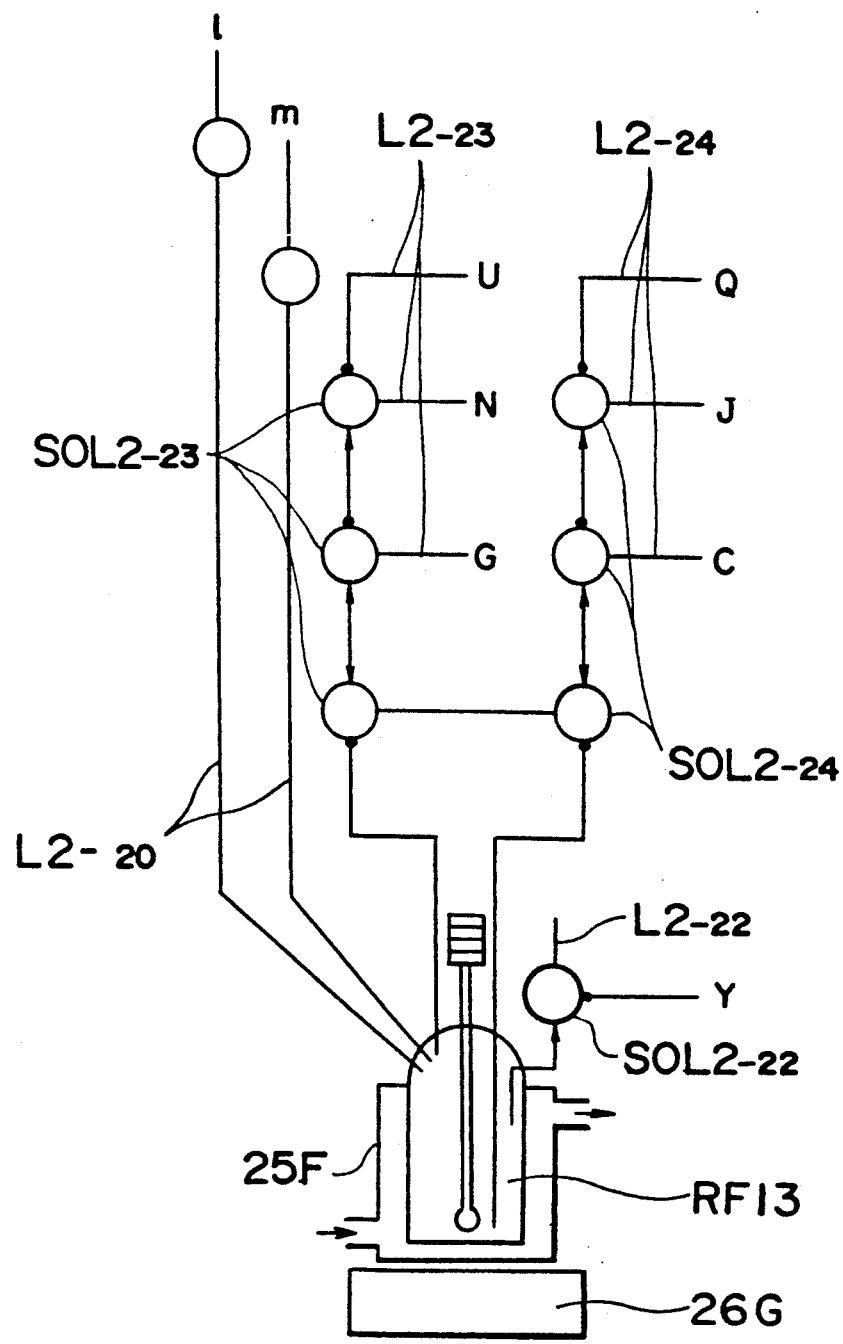
FIG. 17 is a diagram illustrating a pH adjusting flask of the reaction unit used in the apparatus of FIG. 14.
Figure 18:
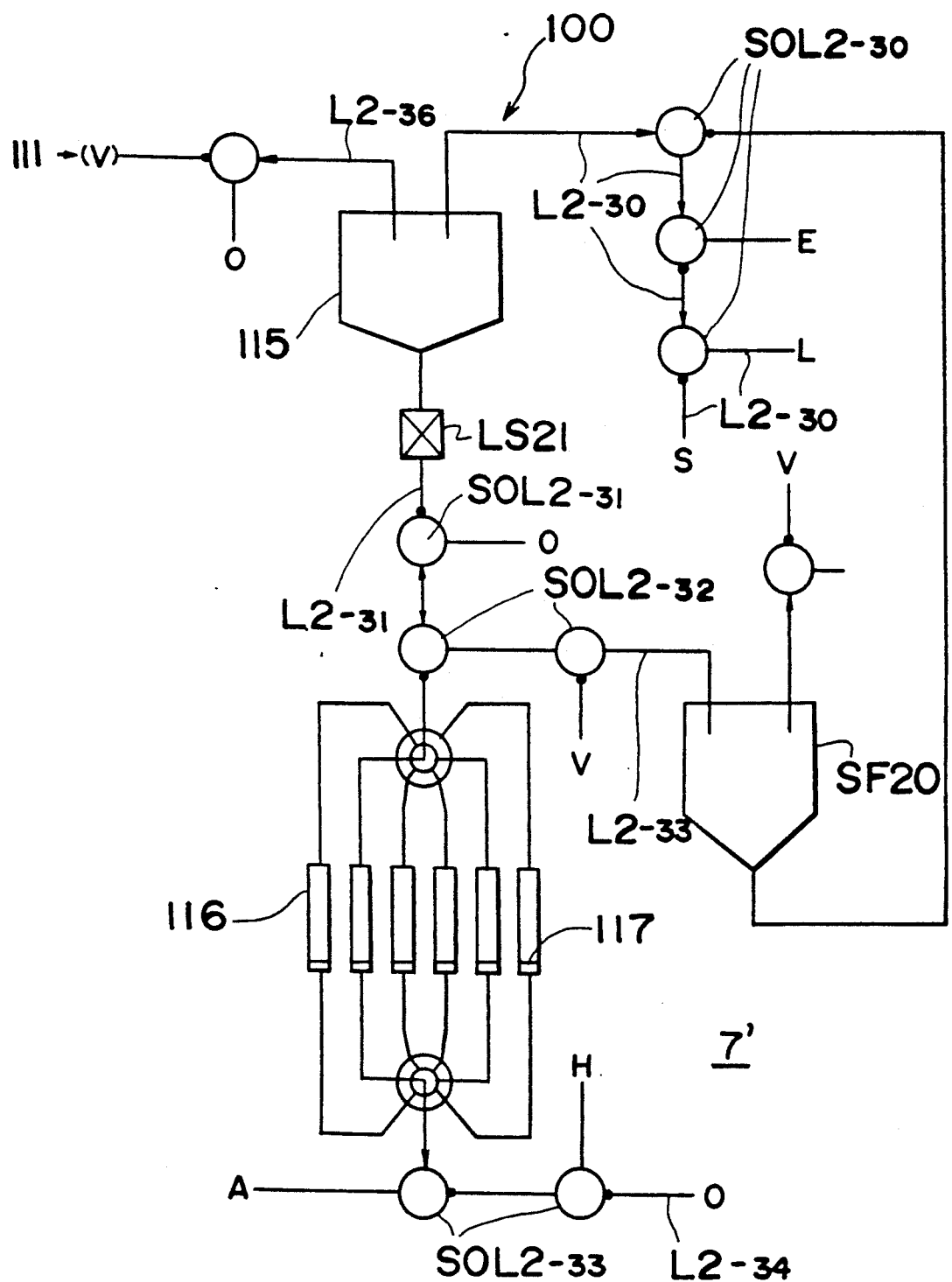
FIG. 18 is a diagram illustrating an extraction/drying device added to the reaction unit employed in the apparatus of FIG. 14.
Figure 19:
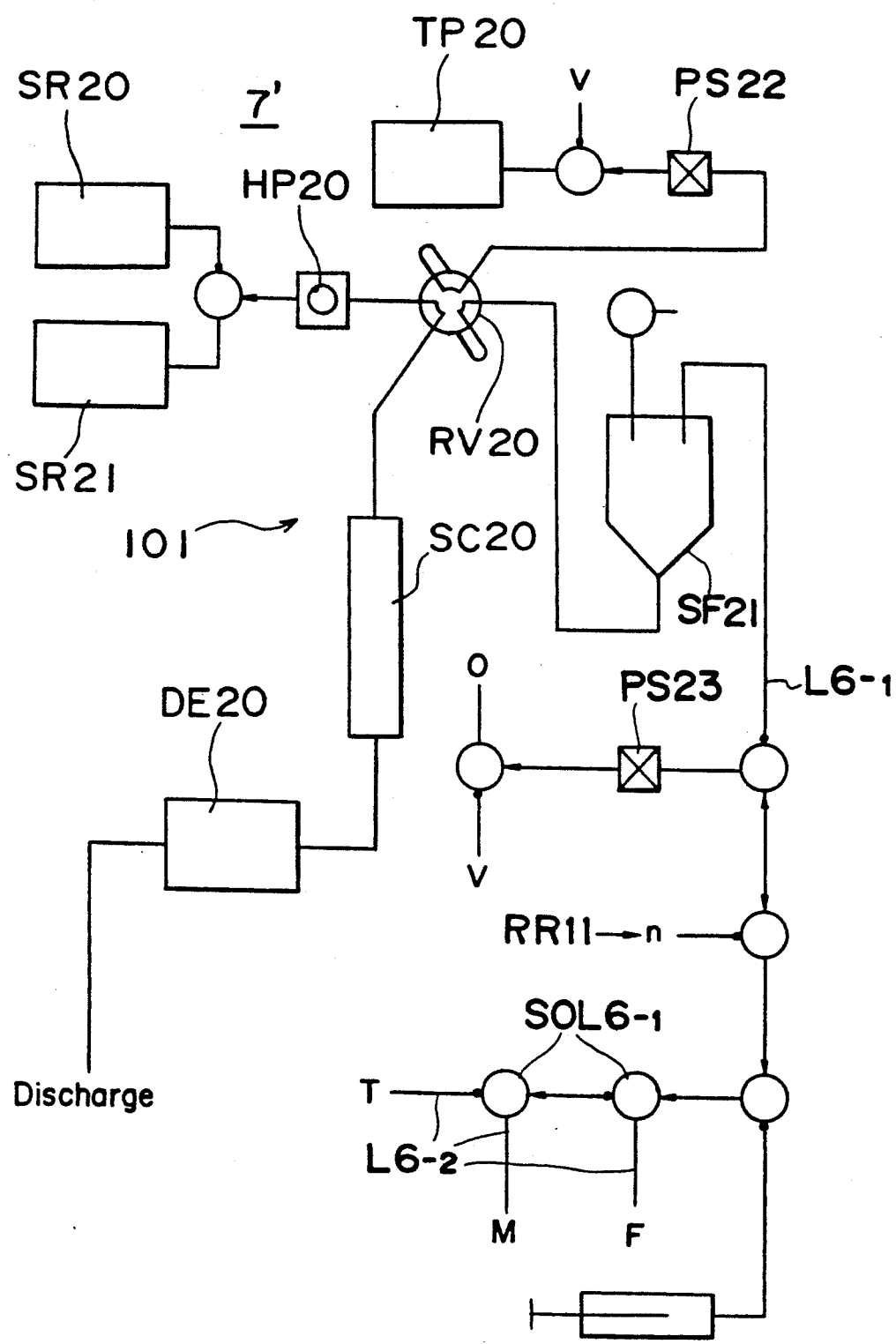
FIG. 19 is a diagram illustrating a monitoring HPLC device added to the reaction unit employed in the apparatus of FIG. 14.
Figure 20:
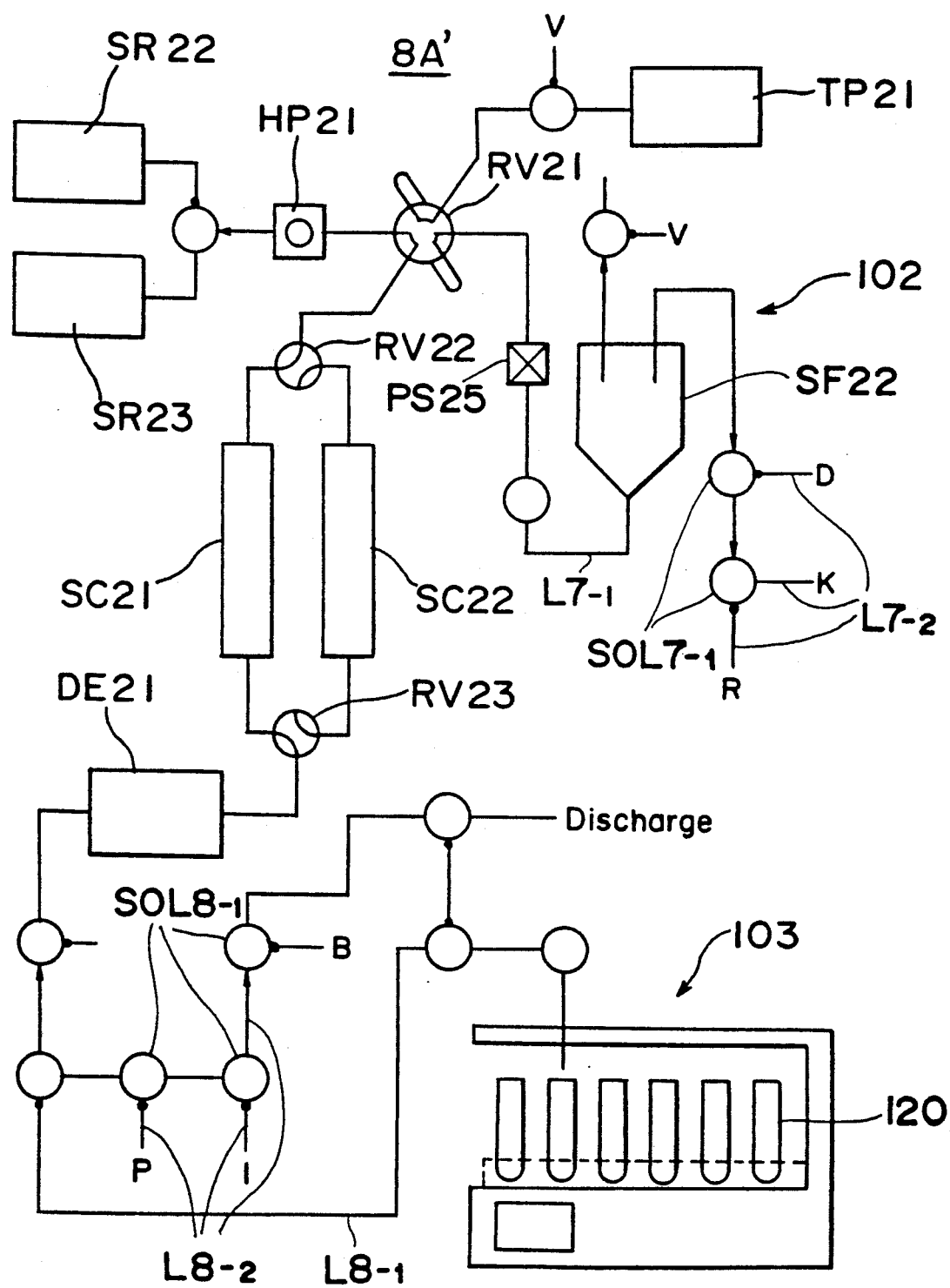
FIG. 20 is a diagram illustrating a purifying unit employed in the apparatus of FIG. 14.
Figure 21:
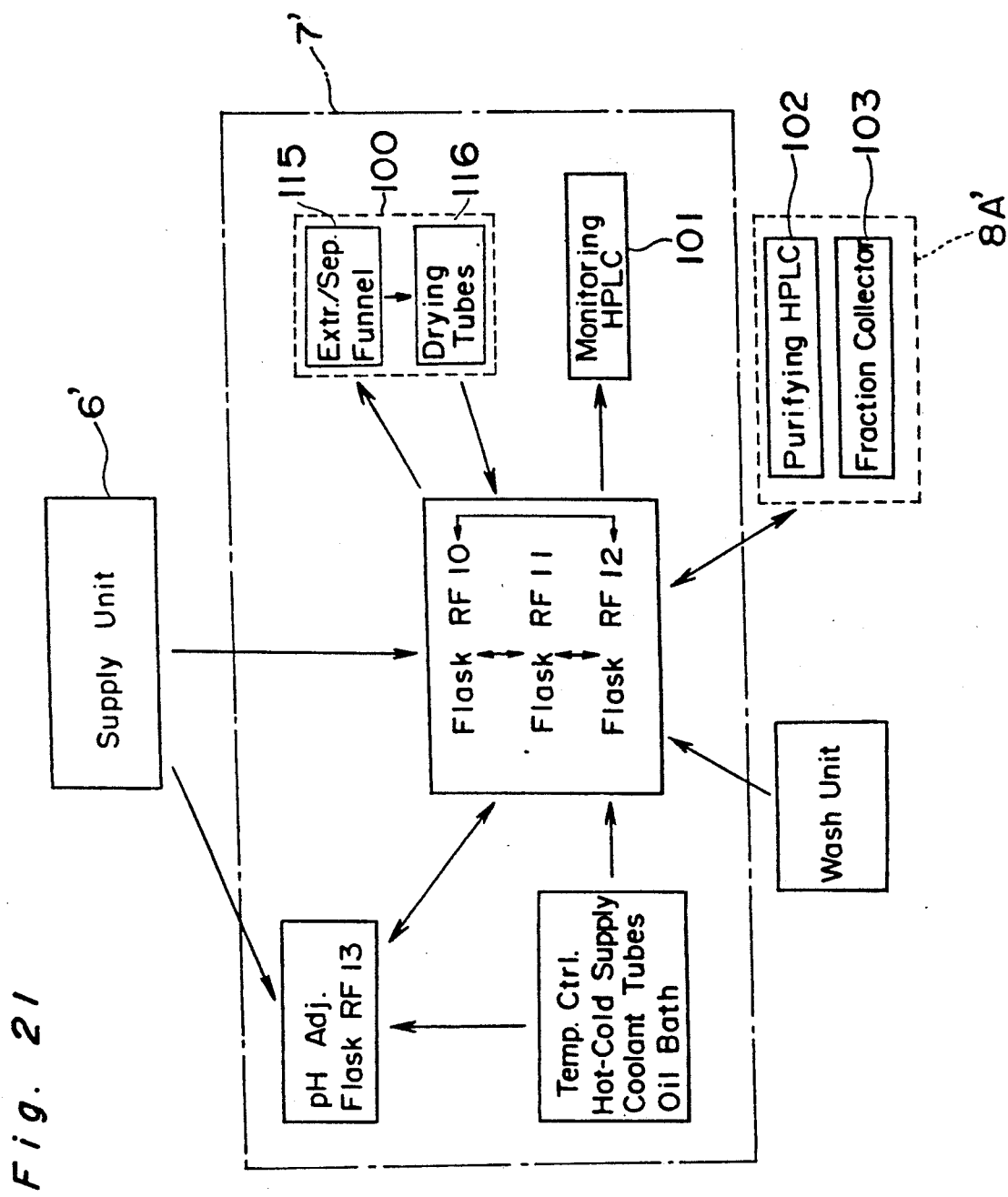
FIG. 21 is a diagram showing the general layout of the apparatus of FIG. 14.

FIG. 14 illustrates the entire system of the synthesizing apparatus (however, the hot-cold circulatory unit, the wash-solvent supply unit and the exhaust/drainage unit are not shown); FIG. 15 illustrates a supply unit 6,; FIG. 16 illustrates the plurality of reaction flasks RF10 to RF12 of a reaction unit 7'; FIG. 17 illustrates the pH adjusting flask RF13 of the reaction unit 7'; FIG. 18 illustrates an extraction/drying device 100 newly added to the reaction unit 7' in accordance with the second embodiment of the present invention; FIG. 19 illustrates a monitoring HPLC device 101 newly added to the reaction unit 7' in accordance with the second embodiment; and FIG. 20 illustrates a purifying unit 102, comprised only of a purifying HPLC 102, and a fraction collector unit 103 connected with the purifying unit 102.

As previously described, in those drawings, the symbols ○ represent a solenoid valve and the symbols ⊠ represent a gas-liquid or liquid-liquid sensor. Characters V and 0 used at free ends of the various lines represent the introduction of a negative pressure and that of a positive pressure, respectively.

The supply unit 6' is, as is the case with the supply unit 6 in the first embodiment, provided with a plurality of reservoirs RR11 to RR26 to which raw materials, reagents and solvents can be automatically supplied from raw materials, reagents or solvents source vessels (not shown). Each of the reservoirs is connected with the associated raw materials, reagents or solvents source bath through a supply line $L1_{-20}$, and a branch line $L1_{-22}$ connected through a solenoid valve $SOL1_{-20}$ to a common suction line $L1_{-21}$ is connected with the respective reservoir. The line $L1_{-21}$ is connected with a diaphragm pump 111 and, by driving the pump 111 and also by activating the solenoid valve $SOL1_{-20}$ corresponding to one of the reservoirs RR11 to RR26 to which the raw material is desired to be supplied thereby to introduce a negative pressure into such one reservoir, the raw materials, reagents or solvents can be automatically supplied from the associated raw materials, reagents or solvents source vessels to the respective reservoirs.

A liquid take-out line $L1_{-23}$ is connected to a lower end of each reservoir and those take-out lines $L1_{-23}$ are bundled into two to three groups which are in turn connected through respective solenoid valves $SOL1_{-21}$ with volumetric measuring lines $L1_{-24}$ having volumetric tubes MT20 and gas-liquid boundary sensors PS20 disposed thereon, so that raw materials, reagents or solvents supplied from the associated reservoirs into the lines $L1_{-23}$ can be supplied to the volumetric measuring lines $L1_{-24}$ through the solenoid valves $SOL1_{-21}$ and can be, after the volumetric measurement, supplied to arbitrary flasks of the reaction unit 7' by the effect of suction developed in the lines. While in the first embodiment of the present invention one volumetric tube MT and one gas-liquid boundary sensor PS have been described as installed on each of the volumetric measuring lines $L1_{-24}$, two sets of a pair of volumetric measuring tubes $MT20_{-1}$ and $MT20_{-2}$ and two gas-liquid sensors $PS20_{-1}$ and $PS20_{-2}$ are employed for the measurement and detection of the different quantities. By the employment of those plural sets of the volumetric measuring tubes and the sensors, various volumetric measurements can be accomplished for the quick supply of the raw materials, reagents and solvents.

The reservoirs installed in the supply unit 6, are connected with lines $L1_{-27}$ so that raw materials, reagents and solvents can be supplied to any one of the flasks to be installed in the reaction unit 7' as will be described later. In other words, each of the lines $L1_{-27}$ shown in FIG. 15 is connected with lines $L2_{-20}$, which are in turn connected with reaction flasks and pH adjusting flask of the reaction unit 7' shown in FIGS. 16 and 17, in correspondence with a, b, —m, n. Solenoid valves SOL1-$_{24}$ and SOL2-$_{20}$ are disposed on the lines L1-$_{27}$ and L2-$_{20}$ so that, by activating these solenoid valves, arbitrarily chosen reservoirs can be communicated with arbitrarily chosen flasks and, by the introduction of a negative pressure from the diaphragm pump 111 connected with the flasks through lines, required raw materials, reagents, solvents, etc., can be supplied to the respective flask in arbitrarily selected quantities. In the illustrated embodiment, although no design has been made where all of the reservoirs can be connected with all the reaction flasks, this can be accomplished by changing the solenoid valves and/or by the addition of extra lines.

It is to be noted that, in the second embodiment of the present invention, the reservoirs RR11 to RR15 are used for the storage of solvents, the reservoirs RR16 to RR24 are used for the storage of reagents or raw materials, and the reservoirs RR25 and RR26 are used for the storage of pH adjusting liquids. Accordingly, the reservoirs RR25 and RR26 can supply the pH adjusting liquids only to the pH adjusting flasks, as will be described later, of the reaction unit 7' shown in FIG. 17.

Although suction under reduced pressure is effected from the reservoirs to the flasks of the reaction unit, use may be made of a compressor 110 for effecting the supply by purging as shown in FIGS. 14 and 15. It is, however, to be noted that the illustrated compressor 110 is used for supplying air, etc., to the lines during a washing step.

The reaction unit 7' differs from the first embodiment in that three reaction flasks RF10, RF11 and RF12 are employed in the reaction unit 7', to which flasks the raw materials, reagents and solvents can be supplied directly from the arbitrary reservoirs RR11 to RR24 of the supply unit 6, through the lines L1-$_{27}$ and L2-$_{20}$ and in that circulation can be effected among these three reaction flasks RF10, RF11 and RF12 to effect a transfer of a reaction liquid, as will be described later.

The first reaction flask RF10 and the second reaction flask RF11 are similar in construction to each other and also similar in construction to the reaction flask RF provided in the reaction unit 7 in the first embodiment and are provided with circulating jackets 25D and 25E for the circulation of a heating medium or a cooling medium and stirrers 26D and 26E, both of the jackets and stirrers being installed therearound. Also, the reaction flasks RF10 and RF11 in the second embodiment are provided with coolant tubes (condensers) 112A and 112B communicated with the respective interiors thereof. The third reaction flask RF12 is used when heating to a higher temperature than any one of the first and second reaction flasks is desired to be effected, or when the temperature is desired to be arbitrarily adjusted, and is surrounded with an oil bath 113 having a heater 114 installed therein for controlling the temperature as desired up to 200° C. The reaction flask RF12 is also provided with a coolant tube 112C and a stirrer 26F. Accordingly, where reaction is desired to be effected at a relatively low temperature or where no arbitrary change in temperature is necessary, the reaction flasks RF10 and RF11 are used, but where the reaction is desired to be effected at a relatively high temperature or where the temperature is desired to be arbitrarily changed, the reaction flask RF12 is used. Moreover, in order to increase the stirring efficiency, the reaction flasks RF10, RF11 and RF12 are and also with the diaphragm pump 111 through the lines L2-$_{22}$ so that at appropriate times air or an inert gas such as nitrogen, argon, helium, etc. can be supplied to effect a bubbling inside these reaction flasks. The lines L2-$_{21}$ and L2-$_{22}$ are provided with solenoid valves SOL2-$_{21}$ and SOL2-$_{22}$ in correspondence with the reaction flasks so that stirring by bubbling can take place only in the required flasks. It is to be noted that the stirring by bubbling is employed where the mixture within the reaction flasks cannot be satisfactorily stirred with the stirrers 26D to 26F.

As shown in FIG. 17, the pH adjusting flask RF13 parallel with the reaction flasks RF10 to RF12 in the reaction unit 7' is also connected with a heating or cooling medium circulating jacket 25F, a stirrer 26G and a line L2-$_{22}$. The pH adjusting flask RF13 and the reaction flasks RF10, RF11 and RF12 are mutually connected with each other by supply lines L2-$_{23}$ extending from the reaction flasks to the pH adjusting flasks and output lines L2-$_{24}$ extending from the pH adjusting flasks to the reaction flasks so that, after the pH adjustment, the reaction liquid can be transferred to any desired reaction flask. Because of this, on one side adjacent the pH adjusting flask RF13, the lines L2-$_{23}$ and L2-$_{24}$ are provided with solenoid valves SOL2-$_{23}$ and SOL2-$_{24}$ corresponding to the respective reaction flasks so that, by switching these solenoid valves SOL2-$_{23}$ and SOL2-$_{24}$, the mixed liquid within the required reaction flask can be introduced into the pH adjusting flask. It is also possible to transfer the mixed liquid among the reaction flasks RF10, RF11 and RF12 without being passed through the pH adjusting flask RF13. In addition, on the side of the reaction flasks RF10, RF11 and RF12, mixed liquid take-out lines L2-$_{25}$ and the supply lines L2-$_{23}$ are connected together through solenoid valves SOL2-$_{25}$, and, at the same time, re-supply lines L2-26 is connected with the output lines L2-$_{24}$ through solenoid valves SOL2-$_{26}$ so that the removal of the mixed liquid from each of the reaction flasks and the re-supply into each of the reaction flasks can be carried out.

FIG. 18 illustrates an extraction/drying device 100 added to the reaction unit 7' and comprises an extracting/separating funnel 115 and a plurality of parallel drying tubes 116. The extracting/separating funnel 115 is selectively connected with the reaction flasks RF10, RF11 and RF12 through supply lines L2-$_{30}$ and solenoid valves SOL2-$_{30}$ and SOL2-$_{40}$ corresponding to the respective reaction flasks so that the mixed liquid within the predetermined reaction flasks RF10, RF11 and RF12 can be introduced into the extracting/separating funnel 115. An exit at the lower end of the extracting/separating funnel 115 is connected with the drying tubes 116 through lines L2-$_{31}$ having respective sensors LS21 disposed thereon so that an organic layer separated in the funnel 115 can be supplied to the drying tubes 116. Also, in order to carry out a stirring by bubbling within the funnel 115, a line L2-$_{36}$ connected with the diaphragm pump 111 is connected with the funnel 115 and, by opening a solenoid valve SOL2-$_{31}$ disposed on the line L2-$_{31}$, the funnel 115 can be reduced in pressure. In addition, where a water layer separated in the funnel 115 lies beneath the organic layer, a storage bottle SF20 is connected to the line L2-$_{31}$ through a line L2-$_{33}$ for storing the water layer beforehand.

It is to be noted that, where the separated water layer lies above the organic layer, the organic layer is drawn from below into the drying tubes 116 leaving the water layer within the funnel 115. The drying tubes 116 are, as hereinbefore described, connected parallel to each other and can be selectively communicated with the line L2-$_{31}$ on the inlet side and with the re-supply line L2-$_{34}$ connected with the reaction flasks RF10, RF11 and RF12 on the exit side. Each of the drying tubes 116 has a drying agent such as anhydrous sodium sulfate filled therein for dehydrating the organic layer then flowing therethrough and is provided with a glass filter 117 for the removal of insoluble materials. Solenoid valves SOL2-$_{33}$ and SOL2-$_{34}$ are disposed on lines L2-$_{34}$ connecting between the drying tubes 116 and the reaction flasks RF10, RF11 and RF12 so that the reaction liquid having been dried can be returned to the arbitrary reaction flasks. Thus, since the reaction flasks and the extracting/drying device are circulatorily connected with each other, the extracting procedure can be repeated in a desired or required number of times.

FIG. 19 illustrates a monitoring HPLC device 101 added to the reaction unit 7', which device 101 is operable to supply a small quantity of the mixed reaction liquid arbitrarily from the reaction flasks RF10, RF11 and RF12 to analyze and monitor the conditions and progress of the reaction. Accordingly, main lines L6-$_1$ of the device 101 is connected through respective solenoid valves SOL6-$_1$ with lines L6-$_2$ connected to the reaction flasks RF10, RF11 and RF12. The lines L6-$_2$ are connected through solenoid valves SOL2-$_{41}$ to the lines L2-$_{25}$ for the removal of the liquids from the reaction flasks and, accordingly, the mixed reaction liquid can be supplied from the arbitrary reaction flasks to the monitoring HPLC device for the analysis of the reaction conditions. This monitoring HPLC is generally similar in structure and operation to the preparative HPLC of the purification unit 8 used in and described in connection with the first embodiment of the present invention. In other words, the mixed reaction liquid supplied from the reaction flask is stored and diluted to an arbitrary concentration, and is provided with a storage bottle SF21 for the storage of the diluted liquid, a column SC20, HPLC pump HP20, dissolving solution supply sections SR20 and 21, a transfer pump TP20 for introducing a predetermined quantity of sample from the storage bottle SF21 to a sample loop, a six-way rotary valve RV20, a UV absorption detector DE20, and sensors PS22 and PS23.

FIG. 20 illustrates a preparative HPLC 102 for purification. In the second embodiment of the present invention, purification is carried out only with the use of the HPLC 102 and the resultant purified product is supplied to the fraction collector 103 connected therewith.

Supply lines L2-$_{42}$ from the reaction flasks RF10, RF11 and RF12 are connected through solenoid valves SOL7-$_1$ to main line L7-$_1$ of the purifying HPLC 102 so that, by switching the solenoid valves, the reaction liquids can be supplied directly to the purifying HPLC 102 from either the reaction flasks RF10, RF11 and RF12 through the re-supply lines leading to the reaction flasks. The purifying HPLC 102 is generally similar in structure to the monitoring HPLC 101 and comprises a reservoir SF22 for the storage of the liquid from the reaction flasks, columns SC21 and SC22, dissolving liquid supply baths SR22 and SR23, a HPLC pump HP21, a transfer pump TP21 for introducing a predetermined quantity of the reaction liquid into a sample loop, a six-way rotary valves RV21, four-way rotary valves RV22 and RV23, a sensor PS25, and a UV absorption detector DE21. Efluent from the columns SC21 or SC22 is, after having been measured as to the UV absorption by the detector DE21, supplied through supply line L8-$_1$ to the fraction collector 103 and then to a plurality of vessels 120 disposed in the fraction collector 103 for the collection of the final product.

Arrangement is also made that a required product can be taken out from the fraction collector 103 for supply to the arbitrary reaction flasks RF10, RF11 and RF12. Because of this, lines L8-$_2$ connected with the reaction flasks RF10, RF11 and RF12 through solenoid valves SOL8-$_1$ are connected to the above described lines L8-$_1$. Accordingly, supply of the reaction product is possible from any one of the reaction flasks RF10, RF11 and RF12 and the pH adjusting flasks to the purifying HPLC 102 and the supply o the resultant liquid collected in the fraction collector 10 after the purification in HPLC is also possible from the fraction collector 103 to any one of the reaction flasks RF10, RF11 and RF12.

The relationships in connection among the reaction flask RF13, RF11 and RF12, the pH adjusting flasks 13, the extracting/drying device 100, the monitoring HPLC 101, the purifying HPLC 102 and the fraction collector 103 are shown by A, B to T and U in the drawings.

Also in those lines, line filters 130 are disposed in the vicinity of exits of the reaction flasks, portions at which the liquid or the air is introduced or discharged, and also in the vicinity of the various valves.

As hereinbefore described, the second embodiment of the present invention is featured in that the lines are installed through the solenoid valves for the selective opening and closure of the associated lines so that the raw materials, reagents and solvents can be supplied from the supply unit 6' to any one of the reaction flasks of the reaction unit and in that circulation is possible from the reaction flasks RF10, RF11 and RF12 to the pH adjusting flask RF13, the extracting/drying device 100, the monitoring HPLC 101, the purifying HPLC 102 and the fraction collector 103 and vice versa. Accordingly, the required operating procedures can be repeated in a desired number of times and unnecessary steps can be dispensed with while allowing the reaction of interest to be readily proceed.

Also, since the reaction unit is provided with the oil bath 113 having the coolant tube (a condenser) 112A-112C and the heater 114 for heating to a relatively high temperature, in place of the technique of circulating the heating medium or the cooling medium, and since the bubbling induced by the blow of the air or the like is employed for accomplishing the stirring, the rate of reaction taking place within the reaction flasks can be accelerated.

Hereinafter, results of experiments conducted with the use of the apparatus according to the second preferred embodiment of the present invention will be illustrated.

EXPERIMENTAL 3

Figure 22:
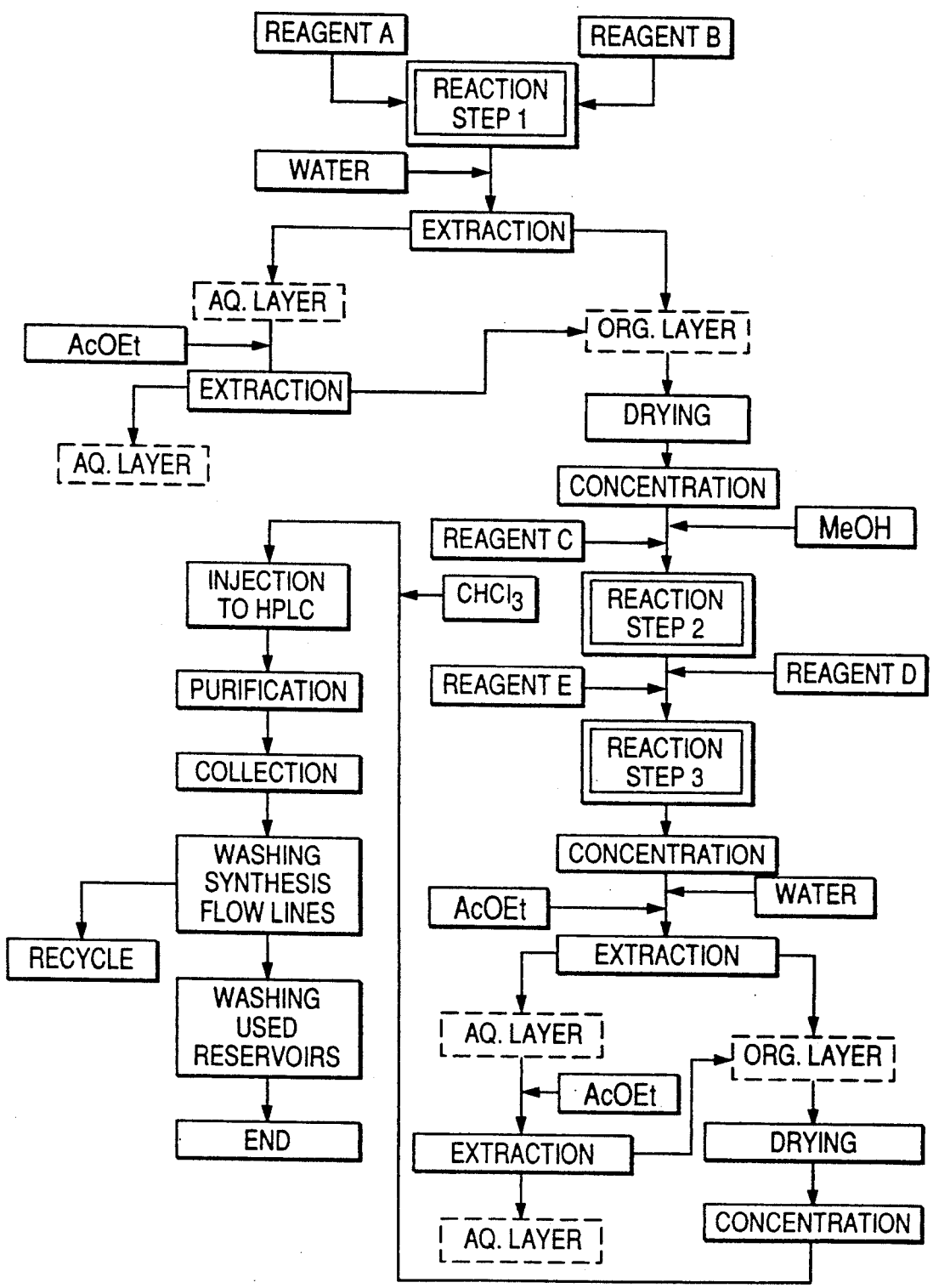
FIG. 22 is a flow chart showing the sequence of procedures carried out by the apparatus of FIG. 14.

This experiment is directed to the synthesis of a final product F with the use of raw materials (reagents) A and B according to the flow chart shown in FIG. 22. It is, however, needless to say that by combining the steps in a desired manner, it can be made to be many steps.

An ether solution, which is the raw material A (15 mmol) and is contained in the reservoir RR16 of the supply unit 6; was quantified to 15 l ml by the use of the volumetric tubes MT20-$_1$ and MT20-$_2$ and the sensors PS20-$_1$ and PS20-$_2$ and was then introduced into the reaction flask RF10. Thereafter, the solution was stirred at 0° C. for 3 minutes. In a similar manner, an ether solution, which is the raw material B and is contained in the reservoir RR18, was quantified to 15 ml (30 mmol) with the use of the volumetric tubes and the sensor and was introduced dropwise into the reaction flask RF10 (at a rate of 10 sec×100 times). The resulting reaction mixture was stirred at 0° C. for 30 minutes, to which water (30 ml), which had been quantified to the volume (10 ml ×3 times) with the use of the volumetric tube and the sensor, was subsequently added. After stirring for 3 minutes, the resulting two-phase mixture was transferred to the extracting/separating funnel 115 of the extracting/drying device 100 with the use of the diaphragm pump 111. After the mixture had been allowed to stand for 3 minutes for the separation of the two-phase mixture into upper and lower layers, the separated upper organic layer was introduced into the reaction flask RF12 through any one of the drying tubes 116 filled with drying agent (anhydrous $Na_2SO_4$, 65 g). Ethyl acetate stored in the reservoir RR13 was introduced into the reaction flask RF10 after having been quantified by the volumetric tube MT20 and the sensor PS20 to 30 ml (10 ml ×3 times). The ethyl acetate solution (30 ml) within the reaction flask RF10 was transferred to the extracting/separating funnel 115 of the extraction/drying device 100, and air was bubbled up through the funnel 115 to help re-extraction and then the separated organic layer was passed through the drying tube 116 before being collected in the reaction flask RF12. The organic solution collected in the reaction flask RF12 was concentrated under reduced pressure at 50° C. for 15 minutes, and methanol from the reservoir RR14 was introduced, after having been quantified by the volumetric tube MT20-2 and the sensor PS20-1, to 10 ml, to dissolve the concentrated residue. An ethanol solution (20 ml, 15 mmol) which is the reagent C and is stored in the reservoir RR23 was introduced into the reaction flask RF12 after having been quantified by the volumetric tubes and the sensors. The resultant reaction mixture was heated with stirring at 70° C. for one hour and then a reagent D (10 ml×2 times, 15 mmol) stored in the reservoir RR15 was added thereto after having been quantified by the volumetric tubes and the sensors. Then, a reagent E (5 ml×4 times, 15 mmol) stored in the reservoir RR24 was, after having been quantified by the volumetric tubes and the sensors, added to the reaction flask RF12. The reaction mixture was refluxed at 100° C. for 90 minutes and then concentrated under reduced pressure at 50° C. Water (30 ml) stored in the reservoir RR11 was added to the residue and ethyl acetate stored in the reservoir RR13 was, after having been quantified by the volumetric tube and the sensor to a predetermined volume (10 ml×3 times), added thereto. After air was bubbled to stir the liquid mixture sufficiently, the reaction mixture was introduced to the extracting/separating funnel 115. The extracting/separating funnel 115 which was previously used had been washed beforehand. After the reaction mixture had been allowed to stand for 3 minutes to separate it into two layers, the separated upper organic layer was passed through any of the drying tubes 116 filled with drying agent (anhydrous $Na_2SO_4$) while the lower water layer was similarly extracted again by the use of 30 ml ethyl acetate. The dehydrated organic layer was then collected in the reaction flask RF11 and concentrated under reduced pressure at 50° C. A solvent (chloroform) stored in the reservoir RR21 was, after having been quantified by the volumetric tubes and the sensors to a predetermined volume (15 ml), introduced into the reaction flask RF11. The mixture was then bubbled with air and stirred to dissolve the residue. The resulting chloroform solution was transferred to the reservoir SF22 of the purification HPLC device 102 and then charged onto the column SC21 of Lichroprop SI-60 (Merck, 25–40 um, 20×500 mm) and eluted first by chloroform and then by a mixture of chloroform : methanol (45:1) to give the target product F.

EXPERIMENTAL 4

The concentrated product obtained in Experimental 3 described above is transferred to the reaction flask RF11. Hot medium liquid heated to 70° C. is circulated through a jacket of the reaction flask RF11 to effect the concentration under reduced pressure (15 minutes). MeOH stored in the reservoir RR14 was, after having been quantified by the volumetric tube and the sensor to 10 ml, transferred to the reaction flask RF11 to dissolve the residue. A reagent stored in the reservoir RR21 was then, after having been quantified by the sensor of the volumetric tube to 5 ml, transferred to the reaction flask RF11. This procedure was repeated four times so that 20 ml in total could be added. Hot medium liquid of 70° C. was circulated to heat the reaction mixture for one hour. A reagent stored in the reservoir RR26 and quantified by the sensor of the volumetric tube to 10 ml was transferred to the reaction flask RF11. This procedure is repeated two times so that 20 ml in total could be added. A reagent stored in the reservoir RR22 and quantified by the sensor of the volumetric tube to 5 ml was then transferred to the reaction flask RF11. This procedure was repeated four times so that 20 ml in total could be added. Hot medium liquid of 70° C. was circulated to heat the reaction mixture for 90 minutes. After the concentration had been effected under reduced pressure while the hot medium liquid was circulated, 30 ml of water was added in a similar manner from the reservoir RR11. Ethyl acetate stored in the reservoir RR13 and subsequently quantified by the sensor PS20 of the volumetric tube MT20 to 10 ml was then transferred to the flask RF11. This was repeated three times so that 30 ml in total could be added. After the bubbling was effected to stir and the extraction was then made, the mixture was transferred to the washed extracting/separating funnel 115. In a manner similar to that described hereinabove, the organic layer was separated and was, after having been passed through the drying tube 116 for drying, transferred to the reaction flask RF12. The water layer was repeatedly extracted and dried with 30 ml of ethyl acetate. While the oil bath of the reaction flask RF12 was heated to 50° C., the concentration was carried out under reduced pressure. $CHCl_3$ (15 ml) stored in the reservoir RR23 and subsequently quantified by the sensors of the volumetric tubes was added to the reaction flask RF12 and the residue was bubbled for stirring to dissolve.

Thereafter, procedures substantially identical with those in Experimental 3 was repeated.

EXPERIMENTAL 5

In the illustrated embodiment, since all of the reservoirs RR11 to RR24 of the supply unit are not connected with the reaction flasks RF10 to RF12, AND change was made in the layout of the lines beforehand so that the reagents and the solvents could be supplied from the reservoirs to the reaction flasks as hereinbelow described.

A reagent stored in the reservoir RR16 and subsequently quantified by the PS sensor of the volumetric tube to 15 ml was transferred to the reaction flask RF12. A reagent stored in the reaction reservoir 18 and subsequently quantified by the sensor of the volumetric tube was transferred to the reaction flask RF12. While this was stirred, a heated circulation was carried out for 60 minutes at 110° C. Water stored in the reservoir RR11 and subsequently quantified by the sensor of the volumetric tube to 10 ml was transferred to the reaction flask RF12. This was repeated three times and 30 ml of water was added to effect the stirring and extraction for 3 minutes. After the reaction mixture had been transferred to the extracting/separating funnel 115 and subsequently allowed to stand for 3 minutes, the resulting upper organic layer was discriminated and separated by the LS sensor. The separated upper layer was then passed through the drying tube 116 having a drying agent (anhydrous $Na_2SO_4$, 6.5 g) filled therein and was then transferred to the reaction flask RF10 in units of limited amounts. Thereafter, ethyl acetate stored in the reservoir RR12 and subsequently quantified by the sensor PS20 of the volumetric tube MT20 to 10 ml was introduced into the reaction flask RF12. This was repeated three times so that 30 ml in total could be transferred to the extracting/separating funnel 115. The separated organic layer was dried in the same manner as that during the previous cycle and was then transferred to the reaction flask RF10.

After the reaction flask RF12 and the extracting/separating funnel 115 were washed with methanol, the extract within the reaction flask RF10 was transferred to the reaction flask RF12. The temperature of the oil bath was set at 50° C. and the concentration was carried out under reduced pressure (for 15 minutes). MeOH' stored in the reservoir RR14 and subsequently quantified by the sensor of the volumetric tube was transferred to the reaction flask RF12 to dissolve the residue. A reagent stored in the reservoir RR19 and subsequently quantified by the sensor of the volumetric tube to 5 ml was transferred to the reaction flask RF12. This was repeated four times to result in the addition of 20 ml in total. While the oil bath 113 was heated to 70° C., a cooling water was circulated through the cooling tube (condenser) 112C and stirred for 60 minutes. A reagent stored in the reservoir RR15 and subsequently quantified by the sensor of the volumetric tube to 10 ml was transferred to the reaction flask RF12. This was repeated two times to result in the addition of 20 ml in total. A reagent stored in the reservoir RR20 and subsequently quantified by the sensor of the volumetric tube to 5 ml was then transferred to the reaction flask RF12. This was repeated four times to result in the addition of 20 ml in total. The reaction mixture was refluxed at 100° C. in the oil bath 113 for 90 minutes.

The subsequent procedures were substantially identical with those in Experimental 3 above.

From the foregoing description, it has now become clear that the automated synthesis apparatus according to the present invention is effective to automatically yield a variety of products from a variety of combination of substituents. This means that, as compared with the prior art in which mass production of one derivative is accomplished by the repetition of definite reaction conditions if the existing plant is automated, the apparatus of the present invention is effective to accomplish a mass production of a variety of derivatives from a small quantity of raw material at different reaction conditions and, therefore, the development of novel pharmaceutical products can be effectively expected automatically. For example, in the first preferred embodiment, since the apparatus of the present invention is fully automated, it can be run for 24 hours a day, and the average rate of synthesis of N-(carboxyalkyl)amino acids can be three compounds daily.

Also, the fact that the synthesis can be accomplished automatically and with no need of manual intervention can greatly contribute to the synthesis of many derivatives of one particular chemical compound. Even if the chemical yields are low under optimum conditions, it is still possible to obtain a sufficient amount of the desired product by repetition of the reaction.

Although the present invention has fully been described in connection with the preferred embodiment thereof with reference to the accompanying drawings, it is to be noted that various changes and modifications are apparent to those skilled in the art. Such changes and modifications are to be understood as included within the scope of the present invention, as defined by the appended claims, unless they depart therefrom.

What is claimed is:

1. An automated synthesizing apparatus comprising:

a supply unit which includes a plurality of reservoirs for containing respective raw material, reagents and solvents, volumetric tubes fluidly connected to said plurality of reservoirs for quantification of the raw material, reagents and solvents, said volumetric tubes have gas-liquid boundary sensors thereon, fluid flow lines extending from said plurality of reservoirs and said volumetric tubes for delivery of raw material, reagents and solvents, and a plurality of solenoid valve assemblies disposed on respective said fluid flow lines for selectively opening and closing said fluid flow lines;

a reaction unit comprising at least one reaction flask device fluidly connected to said fluid flow lines of said supply unit for receiving raw material, reagents and solvents from said supply unit, a separation funnel fluidly connected to said reaction flask device for extracting and washing a reaction liquid transferred from said reaction flask device, a pH adjusting the acidity or basicity of reaction liquid received form said separation funnel, a plurality of additional reagent reservoirs fluidly connected to said reaction flask device for adding a predetermined quantity of reagents to said reaction flask device, a plurality of volumetric tubes for quantification of the reaction liquid and reagents fluidly connected to said reagent reservoirs and said reaction fluidly connected to said reagent reservoirs and said reaction flask device, a plurality of fluid flow lines for delivering the reaction liquid and reagents and solenoid valve assemblies in respective said fluid flow lines for selectively opening and closing said fluid flow lines;

a purification unit connected to said fluid flow lines of said reaction unit for receiving reaction liquid therefrom and comprising at least one of a high performance liquid chromatography device and a centrifugal partition chromatography device, fluid flow lines for delivering a purified product from said purification unit and solenoid valve assemblies in said fluid flow lines for selectively opening and closing said fluid flow lines;

a handling unit connected to said fluid flow lines of said purification unit for handling purified products delivered by said purification unit; and computer control means connected to each of said units, said sensors and said solenoid valve assemblies for controlling the sequence of operation of said units.

2. The automated synthesizing apparatus of claim 1, and further comprising:

a heating medium and cooling medium circulating unit connected with said reaction flask of said reaction unit for supplying a heating medium or a cooling medium to heat or cool said reaction flask of said reaction unit;

a wash-solvent supply unit fluidly connected to a plurality of said units and said fluid flow lines for supplying a wash-solvent thereto for washing said units and said fluid flow lines; and an exhaust drainage unit fluidly connected to a plurality of said units and said fluid flow lines for exhausting wash-solvent and waste materials.

3. The automated synthesizing apparatus of claim 1, wherein said reaction flask device has:

an outer peripheral jacket spaced from said direction flask device to define a gap between said jacket and said reaction flask device for the circulation of a heating medium or a cooling medium;

a stirring means including a plurality of stirrer blades for stirring a reaction liquid within said reaction flask device; and a top opening and a pressure reducing means for reducing the pressure in said reaction flask device connected to said top opening.

4. The automated synthesizing device of claim 1, wherein said handling unit comprises a freeze drying unit for freeze drying purified products received from said purification unit.

5. The automated synthesizing apparatus of claim 1, wherein said purification unit comprises a high performance liquid chromatography device and a centrifugal partition chromatography device for selectively or continuously receiving the reaction liquid for purification.

6. An automated synthesizing apparatus, comprising:

a supply unit having a plurality of reservoirs containing liquids therein, said liquids including raw material, reagents, solvents, and pH adjusting liquids, means for automatically supplying said liquids to said reservoirs from source baths, volumetric tubes having sensors fluidly connected to said reservoirs for quantifying said liquids from said reservoirs, fluid flow lines connected to said reservoirs and said volumetric tubes for delivering said liquids therefrom, and solenoid valves disposed in said flow lines for selectively opening and closing the passages of said fluid flow lines;

a reaction unit comprising a plurality of reaction flasks and a pH adjusting flask, fluid flow lines connecting selected said reservoirs to said reaction flasks, fluid flow lines connecting said reaction flasks to each other and connecting said reaction flasks with said pH adjusting flask to enable recirculation between said reaction flasks and between said reaction flasks and said pH adjusting flasks, an extraction and separation funnel connected with a drying tube having fluid flow lines interconnecting said extraction and separation funnel and said drying tube with said reaction flasks, and a monitoring unit having a high performance liquid chromatography device and fluid flow lines connecting said high performance liquid chromatography device with said reaction flasks for analysis of a reaction liquid from said reaction flasks, said fluid flow lines having respective solenoid valves therein;

a purification unit having at least one of a high performance liquid chromatography device and a centrifugal partition chromatography device connected with said reaction flasks and said pH adjusting flasks by fluid flow lines having respective solenoid valves therein;

a fraction collector unit connected to said purification unit for collecting purified products therefrom and supplying portions of the purified products to said reaction flasks, said fraction collector being connected to said reaction flasks by fluid flow lines having respective solenoid valves; and computer control means connected to each of said units, said sensors and said solenoid valves for controlling the sequence of operation of said units.

* * * * *